(12) United States Patent
Nguyen et al.

(10) Patent No.: US 9,254,144 B2
(45) Date of Patent: Feb. 9, 2016

(54) METHODS AND APPARATUS FOR THROMBECTOMY SYSTEM

(75) Inventors: Hoa D. Nguyen, San Jose, CA (US); Michael S. Mirizzi, San Jose, CA (US)

(73) Assignee: Covidien LP, Mansfield, MA (US)

( * ) Notice: Subject to any disclaimer, the term of this patent is extended or adjusted under 35 U.S.C. 154(b) by 660 days.

(21) Appl. No.: 11/957,238

(22) Filed: Dec. 14, 2007

(65) Prior Publication Data

US 2008/0243153 A1    Oct. 2, 2008

Related U.S. Application Data

(60) Provisional application No. 60/921,122, filed on Mar. 30, 2007.

(51) Int. Cl.
| | | |
|---|---|---|
| *A61B 17/3207* | (2006.01) | |
| *A61B 17/3203* | (2006.01) | |
| *A61B 17/32* | (2006.01) | |
| *A61B 19/00* | (2006.01) | |

(52) U.S. Cl.
CPC ... *A61B 17/320783* (2013.01); *A61B 17/32037* (2013.01); *A61B 2017/320028* (2013.01); *A61B 2019/304* (2013.01); *A61B 2019/481* (2013.01)

(58) Field of Classification Search
CPC .................. A61B 17/32037; A61B 17/22012; A61B 2217/005; A61B 18/1492; A61B 18/245; A61B 2217/007; A61B 17/32078; A61B 17/32032; A61B 2017/320028; A61B 2019/304; A61B 2019/481; A61M 1/008; A61M 3/0283; A61M 1/0058; A61M 1/0064

USPC .................. 604/22, 19, 43; 606/159, 167, 170
See application file for complete search history.

(56) References Cited

U.S. PATENT DOCUMENTS

| | | |
|---|---|---|
| 3,930,505 A | 1/1976 | Wallach |
| 4,493,698 A | 1/1985 | Wang et al. |
| 4,561,439 A | 12/1985 | Bishop et al. |
| 4,646,736 A | 3/1987 | Auth |
| 4,690,672 A | 9/1987 | Veltrup |
| 4,706,687 A | 11/1987 | Rogers |
| 4,715,848 A | 12/1987 | Beroza |
| 4,913,698 A | 4/1990 | Ito |
| 4,998,919 A | 3/1991 | Schnepp-Pesch et al. |

(Continued)

FOREIGN PATENT DOCUMENTS

| | | |
|---|---|---|
| WO | WO 03/007797 | 1/2003 |
| WO | WO 03-096871 | 11/2003 |

OTHER PUBLICATIONS

International Search Report for Application No. PCT-US2008-055520 (the PCT counterpart of the parent application) mailed Jun. 27, 2008.

(Continued)

*Primary Examiner* — Emily Schmidt
*Assistant Examiner* — Lauren M Peng
(74) *Attorney, Agent, or Firm* — Thomas M. Johnston, Esq.

(57) ABSTRACT

In certain embodiments, the system is configured to remove from or fragment materials in a vessel by inserting a catheter into a vessel, wherein the distal tip of the catheter is placed at the surgical site and a liquid spray is applied to materials to remove or fragment (as defined herein) the materials. In certain embodiments, the system comprises a liquid spray emanating from a fragmentation lumen and across a fragmentation opening.

27 Claims, 21 Drawing Sheets

(56) References Cited

U.S. PATENT DOCUMENTS

| | | |
|---|---|---|
| 5,011,488 A | 4/1991 | Ginsburg |
| 5,135,482 A | 8/1992 | Neracher |
| 5,192,268 A | 3/1993 | Shiber |
| 5,259,842 A | 11/1993 | Plechinger et al. |
| 5,261,877 A | 11/1993 | Fine et al. |
| 5,318,518 A | 6/1994 | Plechinger et al. |
| 5,320,599 A | 6/1994 | Griep |
| 5,338,292 A * | 8/1994 | Clement et al. ............... 604/22 |
| 5,419,774 A | 5/1995 | Willard et al. |
| 5,453,088 A | 9/1995 | Boudewijn et al. |
| 5,496,267 A | 3/1996 | Drasler et al. |
| 5,520,635 A | 5/1996 | Gelbfish |
| 5,527,330 A | 6/1996 | Tovey |
| 5,674,226 A | 10/1997 | Doherty et al. |
| 5,713,851 A | 2/1998 | Boudewijn et al. |
| 5,766,194 A | 6/1998 | Smith |
| 5,785,675 A | 7/1998 | Drasler et al. |
| 5,785,678 A | 7/1998 | Griep et al. |
| 5,788,667 A | 8/1998 | Stoller |
| 5,827,229 A | 10/1998 | Auth et al. |
| 5,843,022 A | 12/1998 | Willard et al. |
| 5,846,219 A | 12/1998 | Vancaillie |
| 5,853,384 A | 12/1998 | Bair |
| 5,871,462 A | 2/1999 | Yoder |
| 5,944,686 A | 8/1999 | Patterson |
| 5,989,210 A | 11/1999 | Morris et al. |
| 5,989,271 A | 11/1999 | Bonnette et al. |
| 6,001,078 A | 12/1999 | Reekers |
| 6,135,977 A | 10/2000 | Drasler et al. |
| 6,224,570 B1 | 5/2001 | Le et al. |
| 6,322,533 B1 | 11/2001 | Gonon |
| 6,375,635 B1 | 4/2002 | Moutafis et al. |
| 6,471,683 B2 | 10/2002 | Drasler et al. |
| 6,482,217 B1 | 11/2002 | Pintor et al. |
| 6,558,366 B1 | 5/2003 | Drasler et al. |
| 6,572,578 B1 | 6/2003 | Blanchard |
| 6,635,070 B2 | 10/2003 | Leeflang et al. |
| 6,676,627 B1 | 1/2004 | Bonnette |
| 6,676,637 B1 | 1/2004 | Bonnette et al. |
| 6,719,718 B2 | 4/2004 | Bonnette et al. |
| 6,755,803 B1 | 6/2004 | Le et al. |
| 6,767,353 B1 | 7/2004 | Shiber |
| 6,827,701 B2 * | 12/2004 | MacMahon ......... A61M 1/0009 604/121 |
| 6,926,726 B2 | 8/2005 | Drasler et al. |
| 6,945,951 B1 | 9/2005 | Bonnette et al. |
| 6,984,239 B1 | 1/2006 | Drasler et al. |
| 7,056,315 B2 | 6/2006 | Gonon |
| 2002/0133111 A1 | 9/2002 | Shadduck |
| 2004/0049149 A1 | 3/2004 | Drasler et al. |
| 2004/0204728 A1 | 10/2004 | Haefner |
| 2006/0100606 A1 | 5/2006 | Dobak |
| 2006/0287651 A1 * | 12/2006 | Bayat ........................... 606/51 |
| 2007/0060888 A1 | 3/2007 | Goff et al. |

OTHER PUBLICATIONS

Examination Report from counterpart European Application No. 8731144.5, dated Nov. 2, 2015, 4 pp.

\* cited by examiner

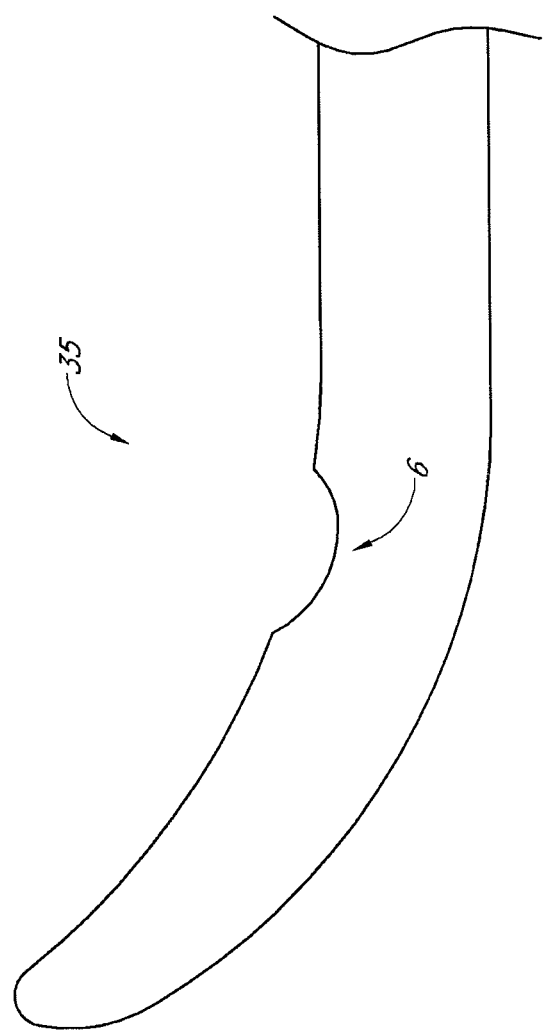

METHODS AND APPARATUS FOR THROMBECTOMY SYSTEM

RELATED APPLICATIONS

This application claims the benefit of priority under 35 U.S.C. §119(e) of U.S. Provisional Application No. 60/921,122, filed on Mar. 30, 2007, entitled METHODS AND APPARATUSES FOR THROMBECTOMY SYSTEM. The foregoing provisional application is hereby incorporated herein by reference in its entirety and is to be considered a part of this specification.

BACKGROUND

1. Field

Certain technologies herein disclosed generally relate to medical devices, and more particularly, relate to medical devices for removal of materials such as a thrombus, or blood clot, from a blood vessel.

2. Description of the Related Technology

A thrombus, or a blood clot, is generally the product of blood coagulation typically due to, for example, poor circulation resulting from an extended sedentary activity. In the early stages of thrombus formation, a thrombus generally has a consistency that is soft, and/or spongy. Over time, a thrombus becomes more tough and fibrotic due to a phenomenon known as the clotting cascade wherein fibrotic tissues increasingly begin to grow into the thrombus. Among other things, a thrombus will decrease blood flow through the affected vessel or in some instance cut-off the flow of blood thereby resulting in the death of tissue supplied by the vessel. Additionally, an embolus is created if a thrombus dislodges from a vessel wall and becomes free-floating. In some cases, an embolus can cause an embolism, or an occlusion of a blood vessel, resulting in, for example, stroke, heart attack or pulmonary embolism.

SUMMARY

In certain embodiments, an apparatus for removing material from a blood vessel lumen comprises a shaft sized for insertion into said blood vessel lumen, said shaft having a fragmentation lumen and a suction lumen; a liquid pressure source in fluid communication with a proximal end of said fragmentation lumen; a suction source in fluid communication with a proximal end of said suction lumen; and a cycling liquid pressure pattern in said shaft, said pressure pattern including (i) a repeating positive pressure impulse in said fragmentation lumen, and (ii) a repeating negative pressure impulse in said suction lumen which alternates with said positive pressure impulse.

In certain embodiments, the liquid pressure source comprises a first pump configured to apply said repeating positive pressure impulse to said fragmentation lumen. In certain embodiments, the suction source comprises a second pump configured to apply said repeating negative pressure impulse to said suction lumen. In certain embodiments, the first pump comprises a reciprocating piston disposed in a cylinder; the piston has an intake stroke and an exhaust stroke; and during the exhaust stroke, the first pump applies the positive pressure impulse to the fragmentation lumen. In certain embodiments, the second pump comprises a reciprocating piston disposed in a cylinder; the piston has an exhaust stroke and an intake stroke; and during the intake stroke, the second pump applies the negative pressure impulse to the suction lumen.

In certain embodiments, the exhaust stroke of the first pump and the intake stroke of the second pump occur during different phases of an operating cycle of the pumps. In certain embodiments, the apparatus further comprises a single motor which drives both said first pump and said second pump. In certain embodiments, the apparatus further comprises a pump drive module; and the pump drive module removably receives the first pump and the second pump. In certain embodiments, the pump drive module comprises a drive coupling which engages the pistons of the first and second pumps to facilitate actuation of the pumps by the pump drive module.

In certain embodiments, the apparatus further comprises a pump drive module; and the first pump and the second pump are non-removably coupled to said pump drive module. In certain embodiments, the pump drive module comprises a pneumatic pump drive. In certain embodiments, the apparatus further comprises a liquid spray emanating from the fragmentation lumen. In certain embodiments, the apparatus further comprises an opening in a distal portion of the shaft, wherein the liquid spray passes across or through said opening. In certain embodiments, the opening is located in a sidewall or at the tip of the shaft.

In certain embodiments, liquid in the fragmentation lumen has a peak pressure of less than 100 PSI just upstream of said spray. In certain embodiments, liquid in the fragmentation lumen has a peak pressure of 20-70 PSI just upstream of said spray. In certain embodiments, liquid in the fragmentation lumen has a peak pressure of 30-50 PSI just upstream of the spray.

In certain embodiments, the spray has a generally cylindrical shape. In certain embodiments, the spray has a generally flat shape. In certain embodiments, the repetition rate of the positive pressure impulse and the negative pressure impulse is variable.

In certain embodiments, an apparatus for removing material from a blood vessel lumen comprises an endovascular shaft having a fragmentation lumen and a suction lumen; a drive unit in fluid communication with said shaft, the drive unit having: a liquid pressure source in fluid communication with the fragmentation lumen; a suction source in fluid communication with the suction lumen; the liquid pressure source configured to apply positive pressure to the fragmentation lumen in a repeating manner; the suction source configured to apply negative pressure to the suction lumen in a repeating manner which alternates with the application of positive pressure to the fragmentation lumen.

In certain embodiments, the liquid pressure source comprises a first pump. In certain embodiments, the suction source comprises a second pump. In certain embodiments, the first pump comprises a reciprocating piston disposed in a cylinder; the piston has an intake stroke and an exhaust stroke; and during the exhaust stroke, the first pump applies the positive pressure to the fragmentation lumen. In certain embodiments, the second pump comprises a reciprocating piston disposed in a cylinder; the piston has an exhaust stroke and an intake stroke; and during the intake stroke, the second pump applies the negative pressure to the suction lumen.

In certain embodiments, the exhaust stroke of the first pump and the intake stroke of the second pump occur during different phases of an operating cycle of the pumps. In certain embodiments, a reciprocation rate of the first pump and the second pump is variable. In certain embodiments, the apparatus further comprises a liquid spray emanating from the fragmentation lumen. In certain embodiments, the apparatus further comprises an opening in a distal portion of the shaft, wherein the liquid spray passes across or through the opening. In certain embodiments, the opening is located in a sidewall or at the tip of said shaft.

In certain embodiments, liquid in the fragmentation lumen has a peak pressure of less than 100 PSI upstream of the spray. In certain embodiments, liquid in the fragmentation lumen has a peak pressure of 20-70 PSI upstream of the spray. In certain embodiments, liquid in the fragmentation lumen has a peak pressure of 30-50 PSI upstream of the spray.

In certain embodiments, a method comprises: during a first portion of an operating cycle, applying positive pressure to liquid in a pressure lumen of a shaft sized for insertion into a blood vessel lumen; during a second portion of said operating cycle, applying negative pressure to liquid in a suction lumen of said shaft; during the first portion of the operating cycle, ceasing the application of negative pressure; during the second portion of the operating cycle, ceasing the application of positive pressure; and repeating the operating cycle a plurality of times.

In certain embodiments, the method further comprises emitting a spray of liquid from the pressure lumen. In certain embodiments, the method further comprises emitting the spray by delivering liquid through the pressure lumen upstream of the spray at a peak pressure of less than 100 PSI. In certain embodiments, the method further comprises emitting the spray across or through an opening in a sidewall or end of the shaft. In certain embodiments, the method further comprises fragmenting endovascular occlusive material with the spray. In certain embodiments, the method further comprises varying a speed of said operating cycle. In certain embodiments, the method further comprises expelling waste material drawn from the suction lumen to a waste container during the first portion of the operating cycle, simultaneously with the applying positive pressure. In certain embodiments, the method further comprises drawing liquid into a pump coupled to the pressure lumen during the second portion of the operating cycle, simultaneously with the applying negative pressure.

In certain embodiments, the ceasing of the application of negative pressure comprises ceasing further application of negative pressure to the suction lumen. In certain embodiments, the ceasing of the application of positive pressure comprises ceasing further application of positive pressure to the pressure lumen.

In certain embodiments, an apparatus for removing material from a blood vessel lumen comprises an catheter shaft sized for insertion into said blood vessel, the shaft having a pressure lumen and an evacuation lumen; liquid flowing through the pressure lumen; a liquid spray emanating from the pressure lumen, the liquid in the pressure lumen having a peak pressure of less than 100 PSI upstream of the spray; the liquid spray being positioned near an opening in the evacuation lumen such that material cut or fragmented by the liquid spray can readily enter the evacuation lumen.

In certain embodiments, the peak pressure is between 20 and 70 PSI. In certain embodiments, the peak pressure is between 30 and 50 PSI. In certain embodiments, the apparatus further comprises a vacuum of 50 mmHg or greater in the evacuation lumen. In certain embodiments, the pressure lumen further comprises a tapered nozzle portion; the liquid spray emanates from the nozzle portion; and the nozzle portion and the liquid spray point toward an interior portion of the catheter shaft. In certain embodiments, the catheter shaft further comprises an opening in a sidewall of the shaft; the liquid spray passes alongside the opening and is the only liquid spray passing alongside the opening; and the liquid spray points toward an interior portion of the catheter shaft. In certain embodiments, the catheter shaft further comprises an opening in a sidewall or tip of said shaft; the liquid spray passes alongside or through the opening and is the only liquid spray passing alongside or through the opening; and the liquid spray emanates distally from the pressure lumen.

In certain embodiments, the pressure lumen further comprises a nozzle portion having a reduced luminal cross-sectional area relative to a proximal portion of the pressure lumen; the liquid spray emanates from the nozzle portion; the catheter shaft further comprises an opening in a sidewall of catheter shaft; the liquid spray passes alongside the opening and the spray passes alongside no other sidewall opening in the shaft. In certain embodiments, the apparatus further comprises a cycling liquid pressure pattern in the shaft, the pressure pattern including (i) a repeating positive pressure impulse in liquid in the pressure lumen, and (ii) a repeating negative pressure impulse in liquid in the evacuation lumen which alternates with the positive pressure impulse.

In certain embodiments, the apparatus further comprises a pressure source configured to apply the repeating positive pressure impulse to the liquid in the pressure lumen, and a suction source configured to apply the repeating negative impulse to the evacuation lumen. In certain embodiments, the pressure source comprises a first pump and the suction source comprises a second pump. In certain embodiments, the pressure lumen further comprises a nozzle portion having a generally circular exit port. In certain embodiments, the pressure lumen further comprises a nozzle portion having an exit port with a flattened shape.

In certain embodiments, a method of removing occlusive material from a blood vessel comprises inserting an elongate shaft into the blood vessel, the shaft having a pressure lumen and an evacuation lumen; applying negative pressure via the evacuation lumen to draw a portion of the occlusive material near the pressure lumen; emitting a liquid spray from the pressure lumen by delivering liquid through the pressure lumen at a peak pressure of less than 100 PSI; and fragmenting the portion of occlusive material with the liquid spray.

In certain embodiments, the method further comprises evacuating the fragmented material via the evacuation lumen. In certain embodiments, the peak pressure is 20-70 PSI. In certain embodiments, the peak pressure is 30-50 PSI.

In certain embodiments, a method comprises delivering liquid through a fragmentation lumen of an elongate shaft sized for insertion into a blood vessel at a peak pressure of 100 PSI or less; emitting the liquid as a liquid spray from the fragmentation lumen; near the liquid spray, applying suction via an evacuation lumen of the elongate shaft. In certain embodiments, the delivering comprises delivering the liquid at a peak pressure of 20-70 PSI. In certain embodiments, the delivering comprises delivering the liquid at a peak pressure of 30-50 PSI. In certain embodiments, the applying suction comprises applying suction of 50 mmHg or more. In certain embodiments, the method further comprises evacuating material fragmented by the liquid spray via the evacuation lumen.

In certain embodiments, a method of removing occlusive material from a blood vessel comprises inserting an elongate shaft into the blood vessel, the shaft having a pressure lumen and an evacuation lumen; applying, in alternating fashion, positive pressure to the pressure lumen and negative pressure to the evacuation lumen; drawing a portion of the occlusive material into the shaft via the negative pressure; and fragmenting the drawn portion of occlusive material via the positive pressure. In certain embodiments, the method further comprises emitting a spray of liquid from the pressure lumen. In certain embodiments, the positive pressure has a peak of less than 100 PSI. In certain embodiments, the method further comprises emitting the spray across or through an opening in a sidewall or end of the shaft.

In certain embodiments, the applying of the positive pressure comprises operating a first pump in fluid communication with the pressure lumen. In certain embodiments, the applying of the negative pressure comprises operating a second pump in fluid communication with the evacuation lumen. In certain embodiments, the first pump comprises a reciprocating piston disposed in a cylinder.

In certain embodiments, an apparatus for removing occlusive material from a blood vessel lumen comprises a shaft sized for insertion into said blood vessel lumen, the shaft having a fragmentation lumen and a suction lumen; the shaft having a fragmentation opening in a sidewall thereof, the fragmentation opening being sized to admit at least a portion of the occlusive material through the fragmentation opening; the fragmentation opening being tilted relative to a longitudinal axis of the shaft such that a lengthwise dimension of the fragmentation opening is non-perpendicular to and non-parallel with the longitudinal axis of the shaft, as the shaft is viewed from the side.

In certain embodiments, the fragmentation lumen includes a spray opening which is located next to an edge of the fragmentation opening. In certain embodiments, the fragmentation opening forms an edge opposite the spray opening, the edge being tilted relative to a longitudinal axis of the shaft such that the edge is non-perpendicular to and non-parallel with the longitudinal axis of the shaft, as the shaft is viewed from the side. In certain embodiments, the apparatus further comprises a liquid spray emanating from the fragmentation lumen and passing across or through the fragmentation opening.

In certain embodiments, the apparatus further comprises liquid under positive pressure in the fragmentation lumen upstream of the liquid spray, the liquid being at a peak pressure of 100 PSI or less. In certain embodiments, the peak pressure is 20-70 PSI. In certain embodiments, the peak pressure is 30-50 PSI. In certain embodiments, the fragmentation opening forms an edge opposite an origin of the spray, the edge being tilted relative to a direction of the spray such that the edge is non-perpendicular to and non-parallel with the direction of said spray.

In certain embodiments, an apparatus for removing occlusive material from a blood vessel lumen comprises a shaft sized for insertion into the blood vessel lumen, the shaft having a fragmentation lumen and a suction lumen; the shaft having a fragmentation opening in a sidewall or tip thereof, the fragmentation opening being sized to admit at least a portion of the occlusive material through the fragmentation opening; the fragmentation opening forming at least one edge having a beveled edge profile.

In certain embodiments, the fragmentation lumen includes a spray opening which is located next to the fragmentation opening. In certain embodiments, the at least one edge having a beveled edge profile is located opposite the spray opening. In certain embodiments, the apparatus further comprises a liquid spray emanating from the fragmentation lumen and passing across or through the fragmentation opening. In certain embodiments, the apparatus further comprising liquid under positive pressure in the fragmentation lumen upstream of the liquid spray, the liquid being at a peak pressure of 100 PSI or less.

In certain embodiments, an apparatus for removing occlusive material from a blood vessel lumen comprises a shaft sized for insertion into the blood vessel lumen, the shaft having a fragmentation lumen and a suction lumen; the shaft having a fragmentation opening in a sidewall or tip thereof, the fragmentation opening being sized to admit at least a portion of the occlusive material through the fragmentation opening; and a generally rigid cutting member extending across the fragmentation opening, the cutting member being configured to cut the occlusive material as it passes through the fragmentation opening.

In certain embodiments, the cutting member comprises at least one wire. In certain embodiments, the fragmentation opening has a lengthwise dimension, and the cutting member extends along said lengthwise dimension. In certain embodiments, the fragmentation opening has a lengthwise dimension, and the cutting member comprises a primary member which extends along the lengthwise dimension, and at least one secondary member which extends from an edge of the fragmentation opening to the first member. In certain embodiments, the apparatus further comprises a liquid spray emanating from the fragmentation lumen and passing across or through the fragmentation opening. In certain embodiments, the apparatus further comprises liquid under positive pressure in the fragmentation lumen upstream of the liquid spray, the liquid being at a peak pressure of 100 PSI or less.

In certain embodiments, an apparatus for removing occlusive material from a blood vessel lumen comprises a shaft sized for insertion into the blood vessel lumen, the shaft having a fragmentation lumen and a suction lumen; the shaft having a fragmentation opening in a sidewall thereof, the fragmentation opening being sized to admit at least a portion of the occlusive material through the fragmentation opening; and a standoff member extending over the fragmentation opening, the standoff member extending radially outward from the fragmentation opening and including at least one standoff opening to permit the occlusive material to pass through the standoff member.

In certain embodiments, the standoff member comprises a dome. In certain embodiments, the dome comprises a wire mesh. In certain embodiments, the dome comprises a perforated polymer. In certain embodiments, the standoff member comprises at least one arch member. In certain embodiments, the apparatus further comprises a liquid spray emanating from the fragmentation lumen and passing across or through the fragmentation opening. In certain embodiments, the apparatus further comprising liquid under positive pressure in the fragmentation lumen upstream of the liquid spray, the liquid being at a peak pressure of 100 PSI or less.

In certain embodiments, a method comprises drawing occlusive material from a vein lumen into a suction lumen of an elongate shaft sized for insertion into a vein; and preventing damage to a valve of said vein located in said vein lumen near said occlusive material. In certain embodiments, the preventing damage comprises employing a standoff member which extends over and radially outward of a fragmentation opening of said shaft. In certain embodiments, the standoff member comprises a dome. In certain embodiments, the standoff member comprises at least one arch member. In certain embodiments, the method further comprises inserting the elongate shaft into the vein lumen before the drawing. In certain embodiments, the valve is located among the occlusive material.

In certain embodiments, the method further comprises positioning a fragmentation opening of the shaft near the occlusive material in the vein lumen; wherein drawing the occlusive material comprises drawing the occlusive material through the fragmentation opening. In certain embodiments, the method further comprises directing a liquid spray across or through the fragmentation opening. In certain embodiments, the method further comprises fragmenting the occlusive material with the liquid spray. In certain embodiments, the drawing occlusive material into the suction lumen comprises drawing the occlusive material through one or more fragmentation openings in the shaft; and the preventing damage comprises preventing the region of the shaft near the one or more fragmentation openings from adhering to the valve.

In certain embodiments, the method further comprises positioning the one or more fragmentation openings near the occlusive material in the vein lumen. In certain embodiments, the drawing occlusive material into the suction lumen comprises drawing the occlusive material through one or more fragmentation openings in the shaft; and the preventing damage comprises preventing the valve from entering any of the one or more fragmentation openings. In certain embodiments, the method further comprises positioning the one or more fragmentation openings near the occlusive material in the vein lumen. In certain embodiments, the drawing the occlusive material comprises drawing the occlusive material through a fragmentation opening located in a sidewall of the shaft; and the preventing damage comprises employing a bent or curved distal portion of the shaft, wherein the fragmentation opening is located at an inside portion of the bent or curved distal portion.

BRIEF DESCRIPTION OF THE DRAWINGS

The accompanying drawings, which are incorporated in and constitute a part of this specification, show examples of the several embodiments, however, other embodiments will be apparent to those of ordinary skill in the art from the drawing and the description, both of which serve to illustrate and not limit the several embodiments disclosed herein.

FIGS. 2A, 2B, 2C, 2D, and 2E are transverse sectioned views of the catheter system.

FIG. 18 is a partial top view of a fragmentation lumen having a curved distal end.

DETAILED DESCRIPTION OF THE EMBODIMENTS

The following description and examples illustrate preferred embodiments of the present invention(s) in detail. There are numerous variations and modifications of the invention(s) that are encompassed by their scope. Accordingly, the description of preferred embodiments should not be deemed to limit the scope of the present invention(s).

Methods, systems, and apparatus for removing or fragmenting materials in a vessel (for example, FIG. 1) in a patient or subject using a thrombectomy system are provided. The terms "subject" and "patient" as used herein, refer to animals, such as mammals, including humans, primates, dogs, cats, sheep, cattle, goats, pigs, horses, mice, rats, rabbits, guinea pigs, and the like. The terms "subject" and "patient" are used interchangeably.

The terms "thrombectomy system" or "system" as used herein are merely terms of convenience and should be construed to include without limitation systems configured to remove material from a vessel in the context of various medical procedures, for example, atherectomy, thrombectomy, or other similar procedures. The types of materials or occlusions to be removed by the system include without limitation, for example, thrombi, plaque deposits, calcium deposits, cholesterol crystals, lipids, or the like. In certain preferred embodiments, the system is used to treat an early stage thrombus in veins, for example the large veins of the leg.

The terms "fragmentation" or "fragmenting" or "to fragment" as used herein include without limitation cutting, shearing, slicing, pulverizing, notching, nicking, indenting, dislodging, disintegrating or the like. The term "vessel" includes, without limitation, arteries, veins (including deep veins), or other similar vessels as well as vessels having or including an implanted stent, graft, or shunt.

Figure 1:
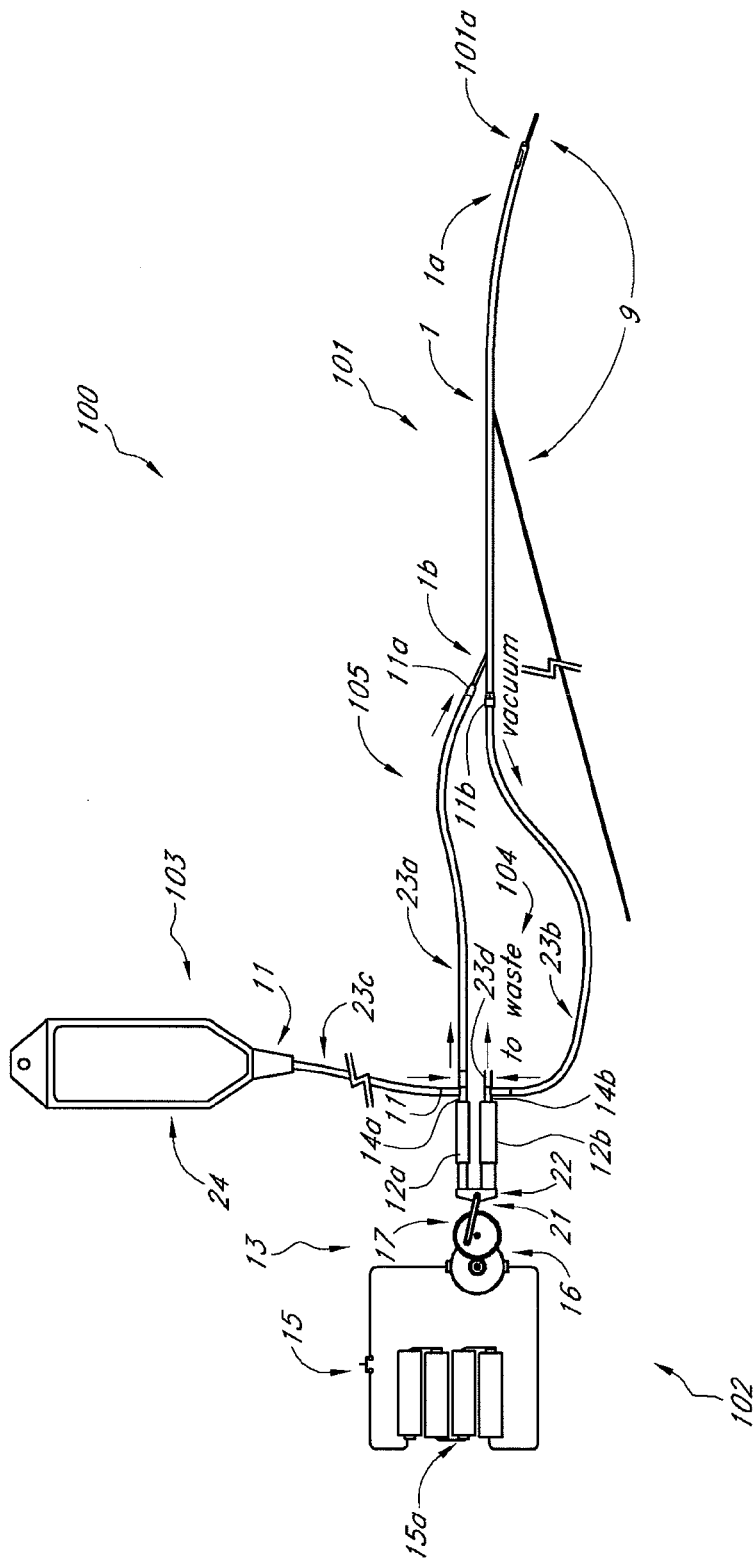
FIG. 1 is a plan view of thrombectomy system for removing material from a vessel lumen.
Figure 2:
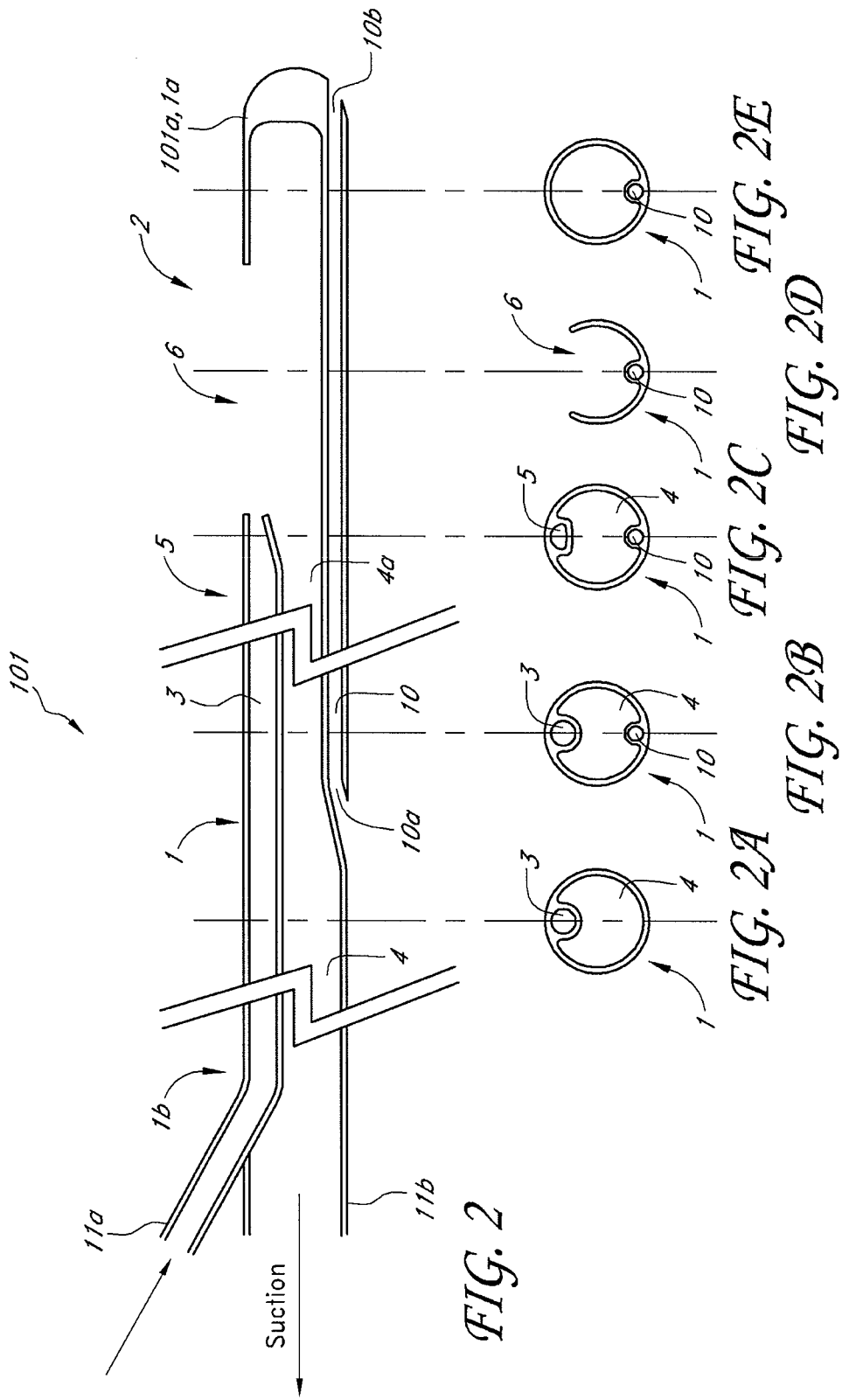
FIG. 2 is a longitudinal sectioned view of a catheter system.

In certain illustrative embodiments, for example FIGS. 1 and 2, the thrombectomy system 100 comprises a catheter system 101, a drive unit 102, a liquid source 103, a waste receptacle 104, and a tubing system 105. Liquid from the liquid source 103 can be provided through the tubing system 105 to the drive unit 102 which can direct the liquid into the catheter system 101. The catheter system 101 can be configured for insertion into a vessel such that a distal end 101a of the catheter system 101 is positioned at a surgical site and a pressurized liquid spray 7 (for example, FIG. 4) is released to cut or fragment a thrombus 8. Additionally, in certain embodiments, the drive unit 102 is configured to evacuate materials and/or liquid from the catheter system 101 and direct the materials and/or liquid through the tubing system 105 into the waste receptacle 104.

FIGS. 2-2E illustrate one embodiment of the catheter system 101 comprising a shaft 1 having a distal end 1a and a proximal end 1b, and an active portion 2 located at or near the distal end 1a. The depicted shaft 1 further comprises a fragmentation lumen 3 that extends distally from a fragmentation lumen connection 11a to a nozzle 5, generally parallel to a suction lumen or evacuation lumen 4, which extends distally from a suction lumen connection 11b toward a suction lumen opening 4a near the nozzle 5. In the embodiment depicted in FIG. 2, the active portion 2 of the shaft 1 comprises a fragmentation opening 6 formed in a sidewall of the shaft 1, the nozzle 5, positioned adjacent the fragmentation opening 6, and the suction lumen opening 4a. The fragmentation opening 6 can comprise an opening having any suitable size or shape (for example rectangular, square, circular or the like), or a window, or a slit or the like in the sidewall of the shaft 1. When the system 100 is in operation, pressurized liquid is directed through the fragmentation lumen 3 such that the liquid spray 7 emanates from the nozzle 5 and across or through the fragmentation opening 6 (for example, FIG. 4). In certain embodiments, the liquid spray 7, which can include a liquid jet or the like, comprises a certain shape, for example, a cylindrical shape, a round shape, an oval shape, a flat shape, a fan shape, a narrow shape, or a wide shape, or any other variation and/or combination of the foregoing. The nozzle 5 can be appropriately configured, e.g. with a broad, flat opening, to generate the desired liquid spray shape.

The catheter system 101 can optionally include radiopaque materials or like pigments in the material or on the surface of the catheter system 101 to enable visualization of the position of the catheter system 101 within the vessel. With reference to FIGS. 1 and 2-2E, the catheter system 101 further comprises, in some embodiments, a guide wire 9 and a guide wire lumen 10 located in the shaft 1 and configured to receive the guide wire 9. The guide wire lumen extends distally from a proximal end 10a to a distal end 10b, generally parallel to the pressure lumen 3 and the evacuation lumen 4. Preferably, the proximal end 10a of the guide wire lumen 10 is located well distal of the proximal end 1b of the shaft 1, so that the guide wire lumen 10 extends along only a distal portion of the shaft 1. The guide wire 9 can enter the proximal end 10a of the guide wire lumen 10 to facilitate directing the catheter system 101 through a vessel of a patient and to a surgical site.

The fragmentation lumen connector 11a and the suction lumen connector 11b facilitate releasable connection of the catheter system 101 to the drive unit 102 via fragmentation tubing 23a and suction tubing 23b, respectively, of the tubing system 105.

The following represent non-limiting examples of some dimensions that can be employed in constructing the catheter system 101. These dimensions are not required and variation from them is considered to be within the scope of the present disclosure. The catheter shaft 1 and active portion 2 can have an outside diameter in the range of 5 F to 9 F (0.066 inches to 0.118 inches), while the pressure lumen 3 can have an inside diameter of 0.028 inches. The nozzle 5 can have a diameter of 0.010 inches to 0.015 inches at its distal opening, and the fragmentation opening 6 can be 0.200 inches long by 0.060 inches wide.

In the depicted embodiment, the drive unit 102 comprises pumps 12 and a motor system 13. The pumps 12 in the drive unit 102 are configured to direct fluid and other materials in and out of the catheter system 101. In certain embodiments, the drive unit 102 comprises at least a fragmentation pump 12a and a suction pump 12b. The depicted pumps 12 each comprise a cylinder and a piston (although other pump types such as peristaltic pumps may be employed), and the size of pumps 12 can be the same or different.

The drive unit 102 further comprises, in some embodiments, check valve pairs 14a and 14b (e.g., FIG. 19A) to direct the liquid flows in accordance with the functioning of the system 100 described herein. As depicted, the fragmentation-side check valve pair 14a includes a first check valve disposed between the fragmentation pump 12a and the liquid source 103, which permits only one-way flow from the liquid source 103 into the fragmentation pump 12a; and a second check valve disposed between the fragmentation pump 12a and the fragmentation tubing 23a of the tubing system 105, which permits only one-way flow from the fragmentation pump 12a into the fragmentation tubing 23a. The suction-side check valve pair 14b includes a third check valve disposed between the suction pump 12b and the waste receptacle 104, which permits only one-way flow from the suction pump 12b to the waste receptacle 104, and a fourth check valve disposed between the suction pump 12b and the suction tubing 23b of the tubing system 105, which permits only one-way flow from the suction tubing 23b into the suction pump 12b.

Figure 20:
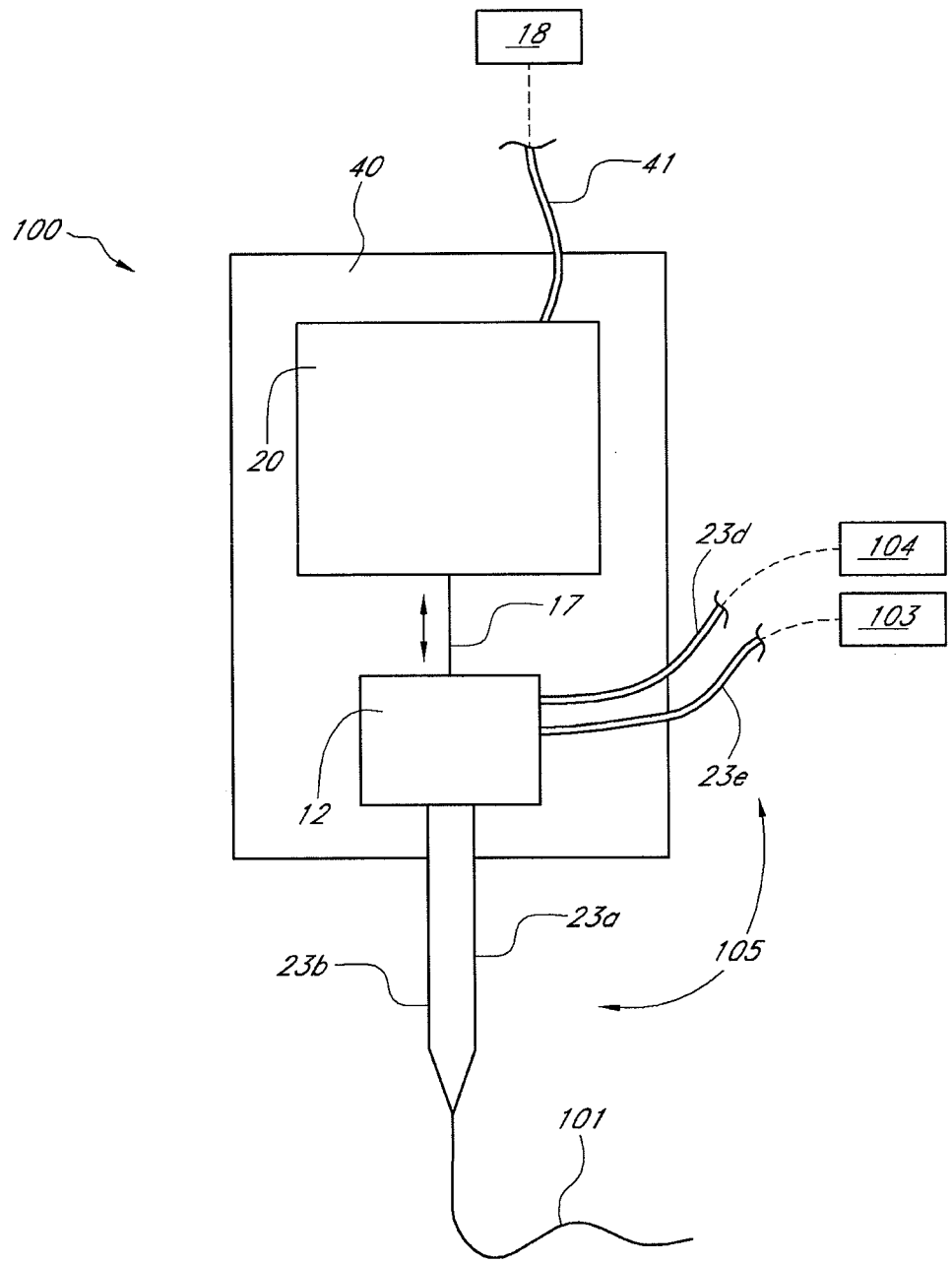
FIG. 20 is a plan view of a disposable integrated reciprocating pneumatic drive, dual pump and catheter system.

Referring again to FIG. 1, the depicted embodiment of the motor system 13 comprises a power source 15, a motor 16, and a linkage mechanism 17. In certain embodiments including that depicted in FIG. 1, the power source 15 is an electrical power source, for example, a plurality of batteries 15a or an electrical outlet such as a typical wall outlet. In other embodiments, the power source 15 is pneumatic; for example, a compressed air source (FIG. 20). The power source provides energy to the motor 16, which can be an electrical motor (for example, FIG. 1) or a pneumatic drive motor (for example, FIG. 20) or the like. In the illustrated embodiment of FIG. 1, the motor 16 connects to the linkage mechanism 17 that is configured to convert rotary motion created by the motor 16 into a reciprocal linear motion to drive a reciprocating arm 21 that engages a dual-piston actuator 22. The dual-piston actuator 22 connects to and drives the pistons of the pumps 12 within the cylinders thereof.

As depicted in FIG. 1, the fragmentation pump 12a connects to both the fragmentation lumen 3 and the liquid source 103 through the fragmentation tubing 23a and fluid source tubing 23c, respectively. In certain embodiments, the liquid source 103 comprises a container 24, such as a bag, tank, etc. The liquid source 103 can alternatively comprise a facility plumbing system. The liquid can include, for example, saline, Ringer's solution, one or more drugs, contrast fluid, or combinations thereof. When employed, the contrast fluid allows for visualization of the thrombus (including the proximal clot face, which can be of particular interest) and the surrounding tissue at the surgical site. Contrast fluid or the like can be delivered to the surgical site through the pressure lumen 3, or through a separate contrast lumen (not shown) integrated into the catheter 101.

In operation, the depicted embodiment of the thrombectomy system 100 cycles between a suction half-cycle and a fragmentation half-cycle. During the suction half-cycle, the drive unit 102 drives the suction pump 12b to generate suction in the suction lumen 4 while drawing liquid from the liquid source 103 into the fragmentation pump 12a. Where the pumps 12 comprise piston pumps, as in the embodiment illustrated in FIG. 1, the drive unit 102 retracts the pistons from the respective cylinders of the suction pump 12b and the fragmentation pump 12a during the suction half-cycle to generate suction and draw liquid from the liquid source in this manner. During the suction half-cycle, the check valve pair 14b permits application of the vacuum created by suction pump 12b to the suction lumen 4 via the suction tubing 23b, while temporarily sealing the suction pump 12b from the waste receptacle 104. The check valve pair 14a allows liquid to be drawn into the fragmentation pump 12a from the liquid source 103 while temporarily sealing the fragmentation pump from the fragmentation lumen 3 and the fragmentation tubing 23a.

Figure 3:
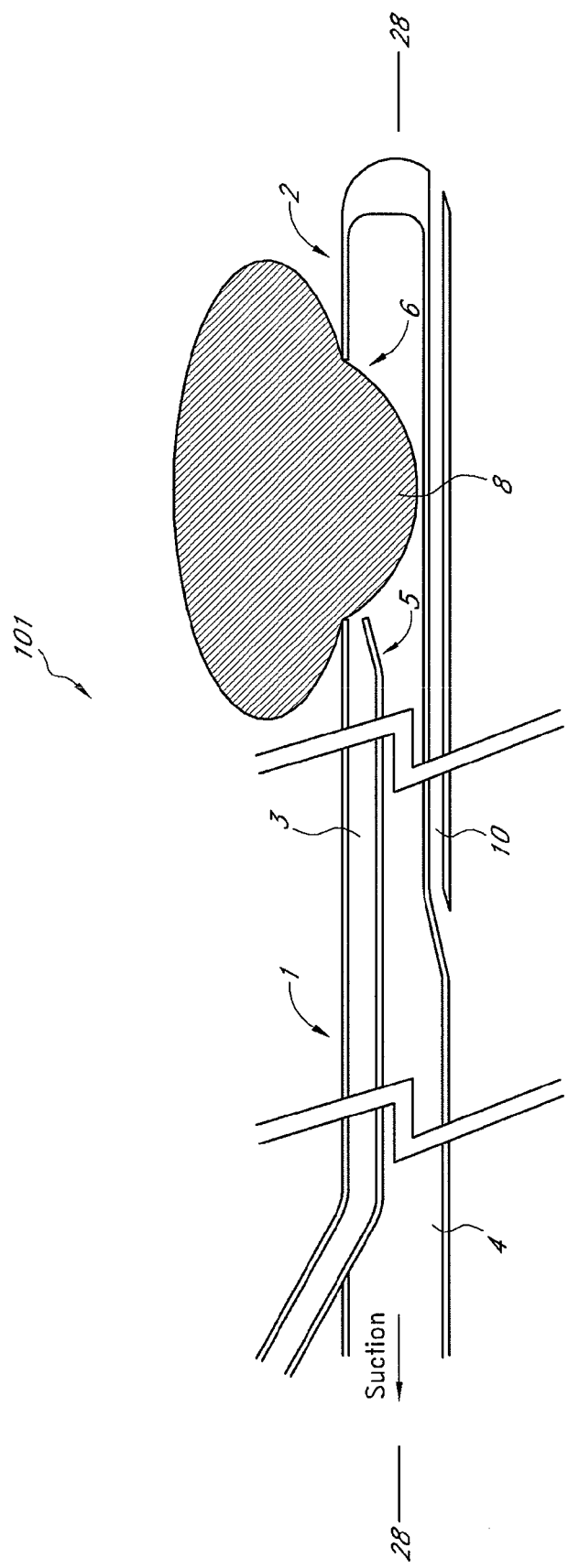
FIG. 3 is a longitudinal sectioned view of the operation of a thrombectomy system comprising a thrombus in a fragmentation opening wherein the nozzle comprises an angled configuration.

As depicted in FIG. 3, the vacuum created by suction pump 12b in the suction lumen 4 draws the thrombus 8 through the fragmentation opening 6 and into the interior of the catheter shaft 1, across the nozzle 5 at the end of the fragmentation lumen 2. Additionally, the vacuum created by the suction pump 12b also draws liquid and other materials through the evacuation lumen, toward or through the suction tubing 23b and the cylinder of the suction pump 12b.

During the fragmentation half-cycle, the drive unit 102 drives the fragmentation pump 12a to generate a pressure in the fragmentation lumen 3. Where the pumps 12 comprise piston pumps, as in the embodiment depicted in FIG. 1, the drive unit 102 advances into the cylinders the pistons of the fragmentation pump 12a and the suction pump 12b, generating fragmentation pressure in the fragmentation pump 12a and expelling to the waste container 104 the liquid and materials within the cylinder of the suction pump 12b. The check valve pair 14a allows the liquid within the cylinder of the fragmentation pump 12a to be directed under pressure into the fragmentation tubing 23a and the fragmentation lumen 3, and through the nozzle 5, while temporarily sealing the fragmentation pump 12a from the liquid source 103. The check valve pair 14b permits the suction pump 12b to expel the liquid and any other materials within the cylinder of the suction pump 12b into the waste receptacle 104, while temporarily sealing the suction pump 12a from the suction lumen 4 and the suction tubing 23b.

Figure 4:
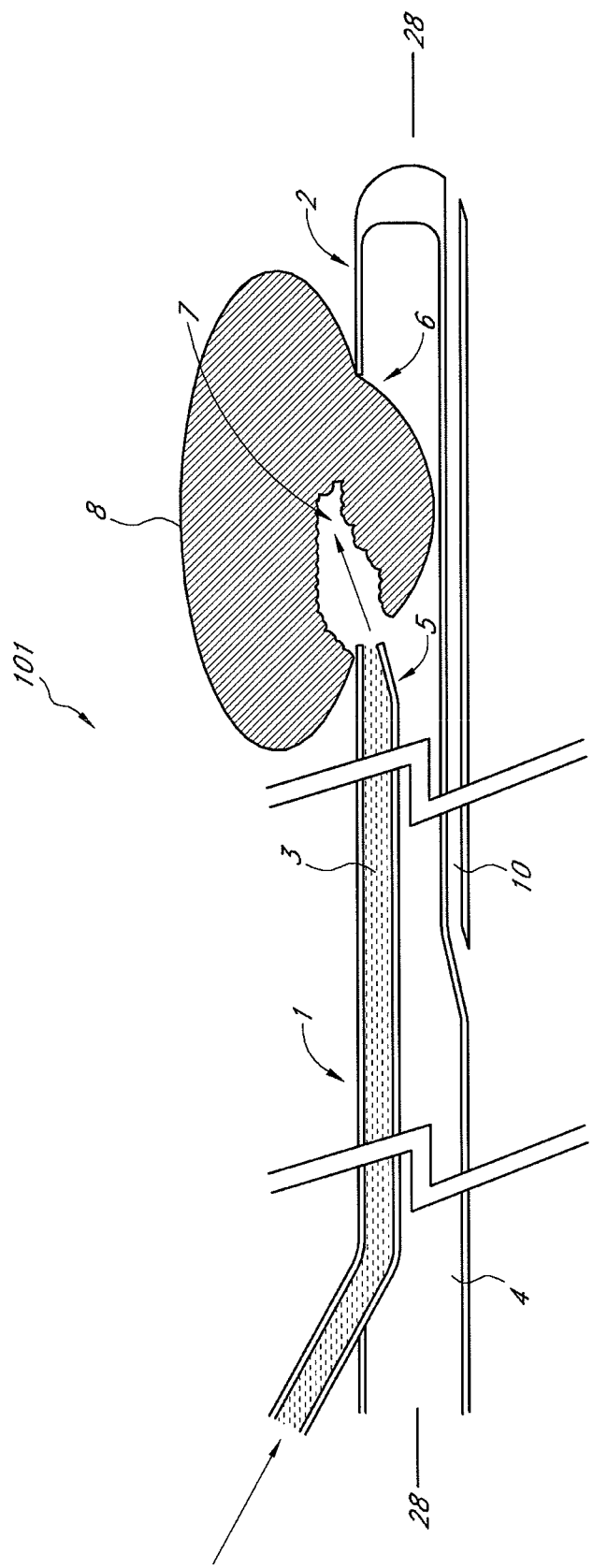
FIG. 4 is a longitudinal sectioned view of the operation of a thrombectomy system showing a liquid spray fragmenting a thrombus wherein the liquid spray is directed at angle.

As seen in FIG. 4, the pressurized liquid directed by the fragmentation pump 12a into the pressure lumen 3 emanates from nozzle 5 as a liquid spray 7 which is configured to fragment, cut, etc. the thrombus 8. The action of the liquid spray 7 causes one or more pieces of the thrombus 8 disposed in the interior of the shaft 1 to break loose from the main mass of the thrombus 8. When the fragmentation half-cycle is complete and the system alternates to the suction half-cycle, the piece(s) fragmented from the thrombus 8 are drawn into the suction lumen 4 and eventually through the suction lumen 4, suction tubing 23b, and suction pump 12b, and into the waste receptacle 104. Through prolonged operation, the system executes a sufficient number of cycles to break up and remove substantially all, or a desired portion of, the thrombus 8.

In the embodiment depicted in FIGS. 3-4, the nozzle 5 is tilted relative to the longitudinal axis of the shaft 1 such that the liquid spray 7 is also tilted relative to the longitudinal axis. The liquid spray 7 thus passes radially outward and through the fragmentation opening 6 as depicted in FIG. 4. Such a liquid spray 7 can pass or cut into the thrombus 8, facilitating the removal of larger pieces and faster removal of the thrombus 8. As will be discussed in greater detail below, alternative configurations of the nozzle 5 and liquid spray 7 can be employed in other embodiments.

In certain embodiments, the thrombectomy system 100 is configured to alternate continuously between the suction half-cycle and the fragmentation half-cycle. The resulting repeating pressure pattern can include a repeating positive peak pressure in the fragmentation lumen 3. The repeating peak pressure in the fragmentation lumen 3 (e.g., as measured just upstream of the nozzle 5) can have a magnitude of less than 100 PSI, 20-70 PSI, or 30-50 PSI in various embodiments.

The repeating pressure pattern can further include a vacuum or negative pressure of 50 mmHg or greater in the suction lumen 4. In certain such embodiments, a vacuum of some magnitude (e.g., peaking in the range 50 mmHg or higher) is continuously present in the suction lumen 4 while the thrombectomy system 100 is in operation, even though the suction pump 12b applies vacuum only during the suction half-cycle as described above. The presence of a check valve between the suction pump 12b and the suction lumen 4 advantageously facilitates the maintenance of a vacuum in the suction lumen 4 when no suction is being applied by the pump 12b.

In certain embodiments, the ceasing of the application of positive pressure during the suction half-cycle comprises ceasing further application of positive pressure to the fragmentation lumen 3 such that a some pressure remains within the fragmentation lumen but that the pressure level therein does not increase during the ceasing. In certain embodiments, the ceasing of the application of vacuum or negative pressure during the fragmentation half-cycle comprises ceasing further application of negative pressure to the evacuation lumen 4 such that a some vacuum remains within the suction lumen 4 but that the vacuum level therein does not increase during the ceasing.

As set forth above, the thrombectomy system 100, in certain embodiments, is configured to cycle or alternate between applying a vacuum to the suction lumen 4 and directing or pulsating a liquid into and through the fragmentation lumen 3. The operating cycle or the alternating can be continuous or intermittent. In still other embodiments, the speed of the alternating is variable, wherein the variability of the alternating speed can be manually controlled by an operator, or automatically and/or dynamically controlled by the thrombectomy system 100 based on at least one factor, for example, whether the system detects thrombus material in the evacuation lumen, or whether the system detects a thrombus, a vessel valve or both at the surgical site or within the fragmentation opening 6.

The alternating use of a suction pump 12b and a fragmentation pump 12a, part of certain embodiments disclosed herein, is advantageous for several reasons. The use of a suction pump 12b allows for selection of the fluid pressure used for fragmenting the thrombus 8 independent of that used for evacuating the removed portions of the thrombus, as opposed to selecting an fluid pressure appropriate for both fragmenting and evacuating the thrombus 8, and/or for drawing the thrombus toward and through the fragmentation window 6. A pressure capable of performing all of these functions is often higher than necessary for cutting the thrombus 8, and thus unnecessarily likely to damage surrounding tissues such as vessel walls. Indeed, in certain embodiments discussed herein, the liquid spray 7 is used for fragmenting the thrombus 8 and not for evacuating the thrombus 8. In these embodiments, the independent selection of the fluid pressure allows the thrombectomy system 100 to operate with a lower fluid pressure.

As discussed above, during the fragmentation half-cycle, the thrombus 8 within the fragmentation opening 6 is fragmented by the liquid spray 7 emanating from the nozzle 5 that is positioned in the active portion 2 of the catheter 101. Various configurations of the active portion 2 are depicted in FIGS. 2-10.

With reference to the embodiment depicted in FIGS. 2-4, the active portion 2 comprises a fragmentation opening 6 and the nozzle 5 that is configured to create a liquid spray 7 directed at an angle relative to the longitudinal axis 28 of the catheter shaft 1. In this embodiment, the fragmentation opening 6 is positioned on the side or the sidewall of the catheter 101 in the active portion 2. Accordingly, the nozzle axis can be configured at an angle relative to the longitudinal axis of the fragmentation lumen 4 as well. In the configuration depicted in FIGS. 2-4, the liquid spray 7 emanates from the nozzle 5 at an angle outward and away from the longitudinal axes of the catheter shaft 1 and the fragmentation lumen 3. A liquid spray 7 that is angled away from the catheter shaft 1 or outward from the fragmentation lumen 4 is useful in removing the thrombus 8 having a tough or hard or fibrous consistency, for example, a chronic thrombus. Alternatively, the angle of the liquid spray 7 can be directed inward into the interior of the catheter shaft 1 in the active portion 2.

Figure 5:
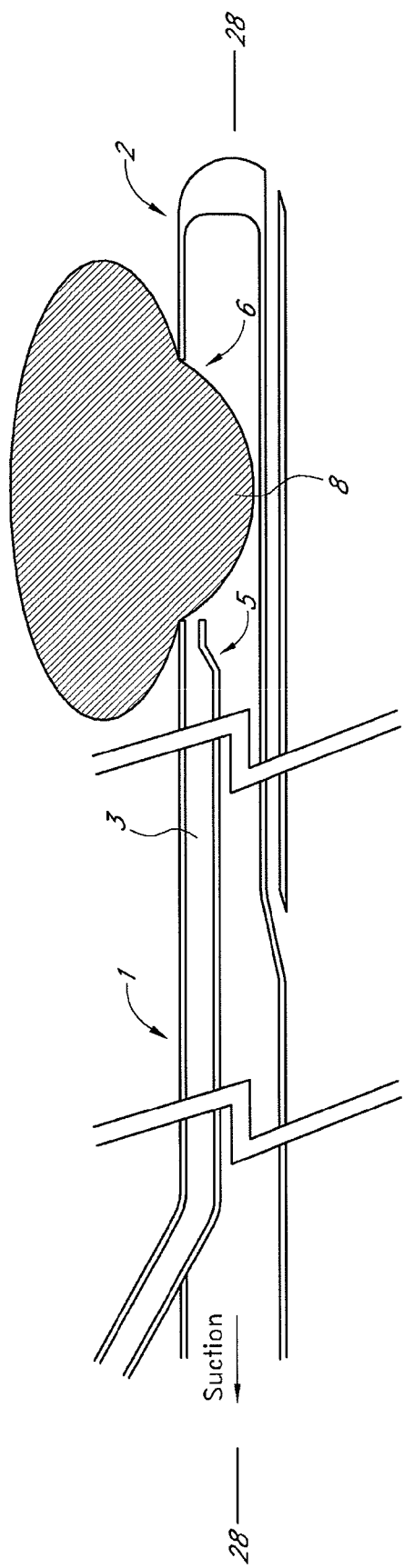
FIG. 5 is a longitudinal sectioned view of the operation of a thrombectomy system comprising a thrombus in a fragmentation opening wherein the nozzle comprises a straight configuration.
Figure 6:
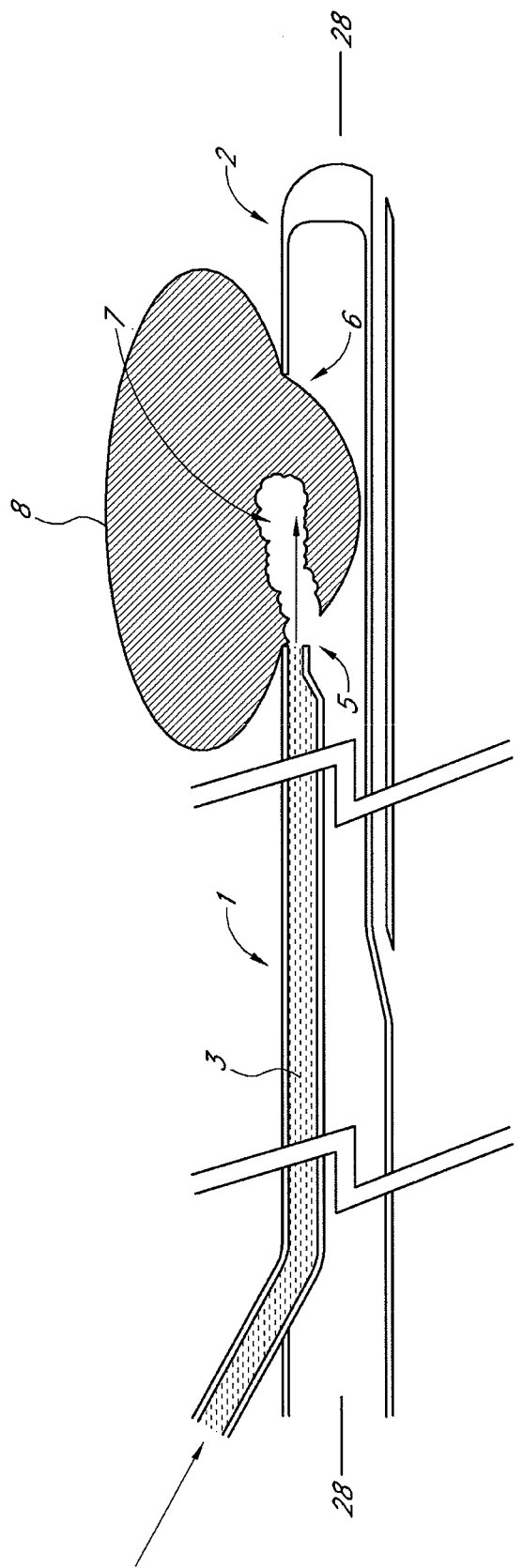
FIG. 6 is a longitudinal sectioned view of the operation of a thrombectomy system showing a liquid spray fragmenting a thrombus wherein the liquid spray is directed straight across the fragmentation opening.

In the active portion 2 depicted in FIGS. 5-6, the axis of the nozzle 5 is substantially parallel to the longitudinal axis 28 of the catheter shaft 1. Similar to the foregoing embodiments, the thrombus 8 is drawn into the fragmentation opening 6 by the vacuum conducted via the suction lumen 4. Additionally, a liquid is directed under pressure through the fragmentation lumen 3 and through the nozzle 5, wherein the liquid spray 7 emanates from the nozzle 5. The liquid spray 7, as depicted in FIG. 6, emanates from the nozzle 5 and is directed across the fragmentation opening 6 in a direction that is substantially parallel to the longitudinal axes of the catheter shaft 1 and the fragmentation lumen 3.

Figure 7:
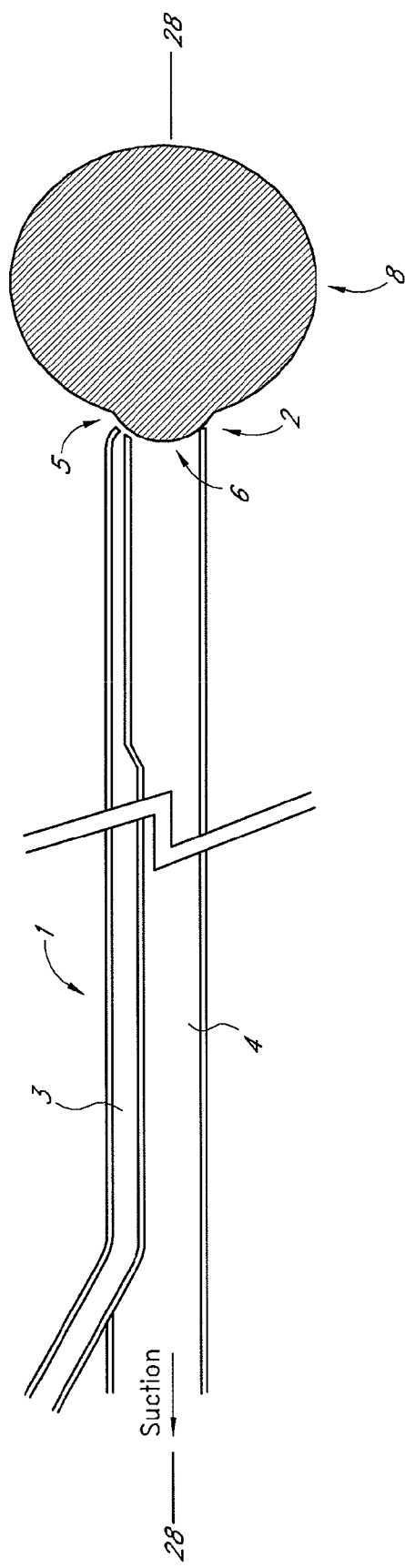
FIG. 7 is a longitudinal sectioned view of the operation of a thrombectomy system comprising a thrombus in a fragmentation opening wherein the fragmentation opening is positioned at the tip of the fragmentation lumen and the nozzle comprises an angled configuration.
Figure 8:
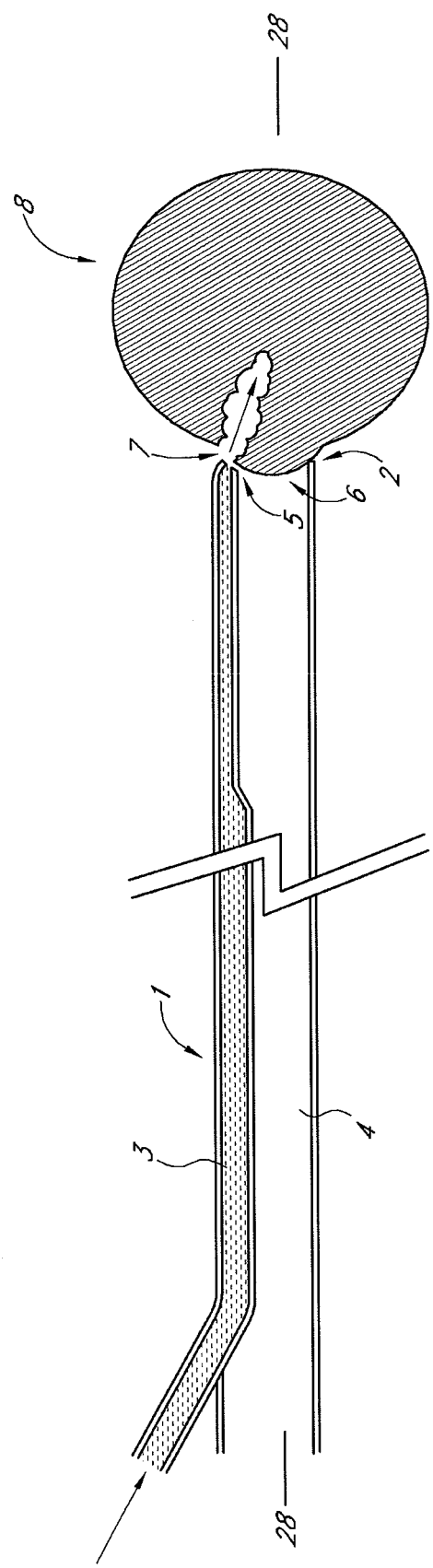
FIG. 8 is a longitudinal sectioned view of the operation of a thrombectomy system showing a liquid spray fragmenting a thrombus wherein the liquid spray is directed at an angle.

In the active portion 2 depicted in FIGS. 7-8, the fragmentation opening 6 is located at the distal end or tip of the catheter shaft 1 and the nozzle 5 has a nozzle axis that is oriented at angle relative to the longitudinal axis 28 of the active portion 2. In this illustrative embodiment, the nozzle axis is directed inward toward the central longitudinal axis 28 of the catheter shaft 1. Alternatively, the nozzle 5 can have a nozzle axis that is substantially parallel to the longitudinal axis of the catheter shaft 1. Similar to the foregoing embodiments, the thrombus 8 is drawn into the fragmentation opening 6 by the vacuum conducted via the suction lumen 4. Additionally, liquid is directed under pressure through the fragmentation lumen 3 and through the nozzle 5, wherein the liquid spray 7 emanates from the nozzle 5. The liquid spray 7, as depicted in FIG. 6, emanates from the nozzle 5 and is directed across the fragmentation opening 6 at an angle relative to the longitudinal axis of the catheter shaft 1. In the depicted embodiment, the nozzle axis is directed radially inward. Additionally, the liquid spray 7 is directed radially inward, across the fragmentation opening 6 and distally into the thrombus 8.

Figure 9:
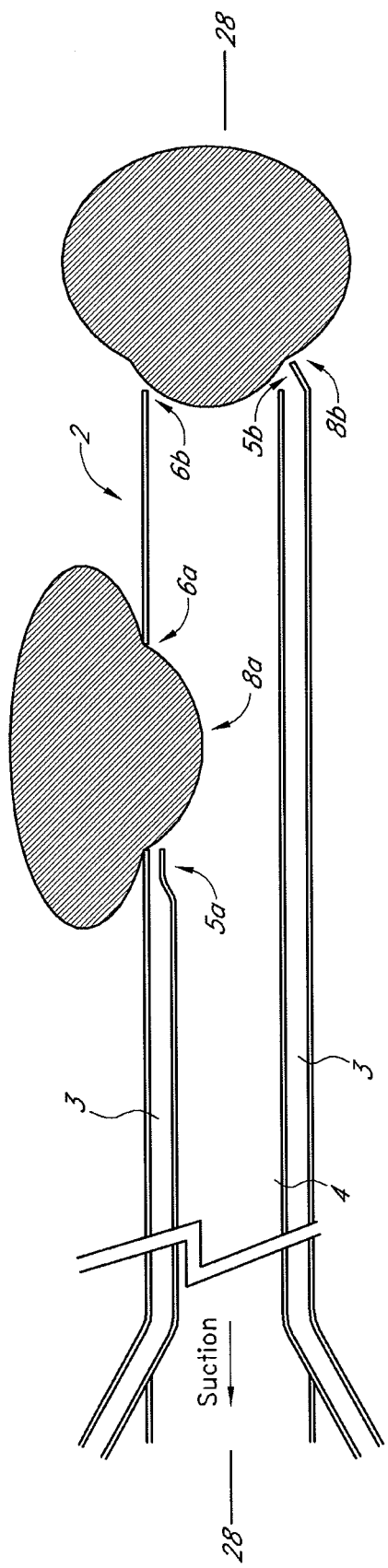
FIG. 9 is a longitudinal sectioned view of the operation of a thrombectomy system comprising multiple fragmentation openings and multiple nozzles having different angle configurations.
Figure 10:
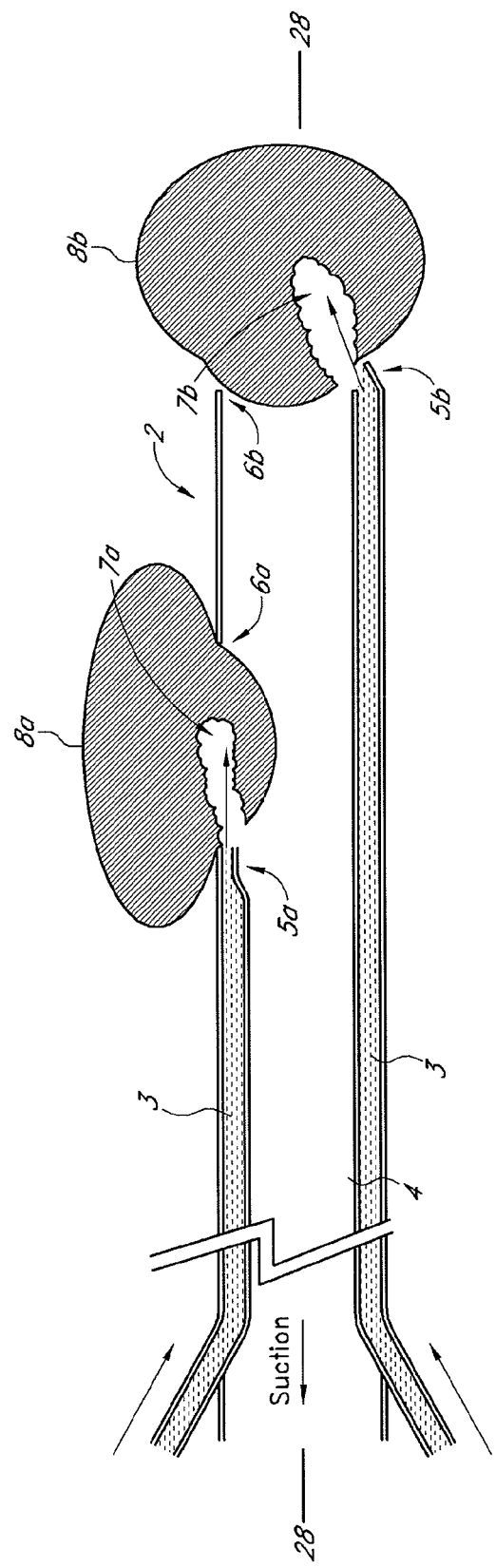
FIG. 10 is a longitudinal sectioned view of the operation of a thrombectomy system showing the fragmentation of multiple thrombi.
Figure 11:
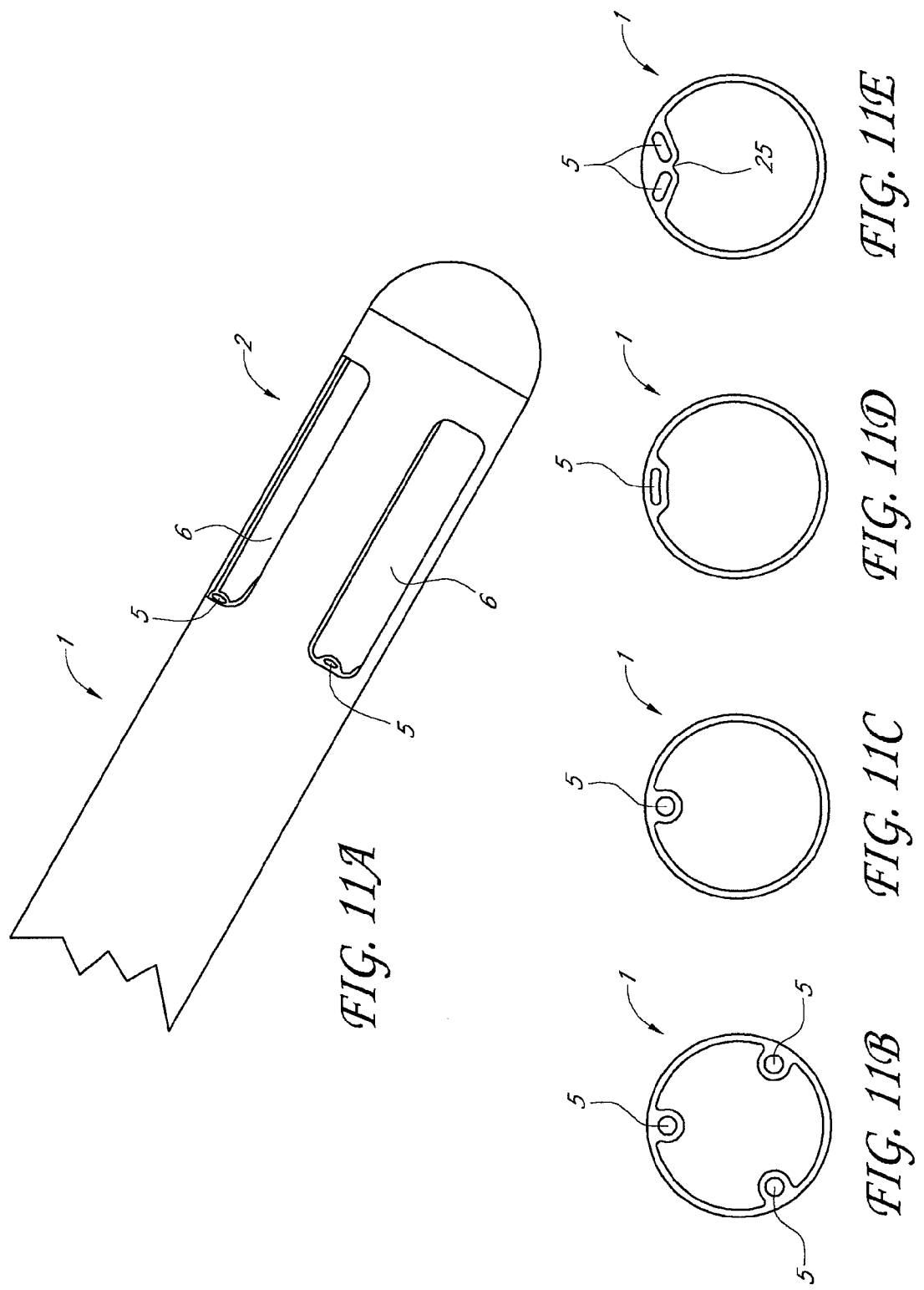
FIG. 11A is a partial side view of a fragmentation lumen having multiple fragmentation openings.
FIGS. 11B, 11C, 11D, and 11E are transverse sectioned views of fragmentation lumens showing various nozzle shape configurations.

In certain embodiments, the active portion 2 comprises multiple fragmentation openings 6 as depicted in FIGS. 9-10 and 11A. In one such embodiment, shown in FIGS. 9-10, the active portion 2 comprises a first fragmentation opening 6a on the side or sidewall of the catheter shaft 1 in the active portion 2 (similar to the embodiment depicted in FIGS. 5 and 6), and a second fragmentation opening 6b at the distal end or tip of the catheter shaft 1 (similar to the embodiment depicted in FIGS. 7 and 8).

As in FIGS. 5-6, the thrombus 8a is drawn into the fragmentation opening 6a by the vacuum provided via the suction lumen 4 during the suction half-cycle, such that during the fragmentation half-cycle the liquid spray 7a emanating from the nozzle 5a is directed across the fragmentation opening 6a and into the thrombus 8a. Similar to FIGS. 7 and 8, the thrombus 8b is drawn into the fragmentation opening 6b by the vacuum provided via the suction lumen 4 during the suction half-cycle, such that during the fragmentation half-cycle the liquid spray 7b emanating from the nozzle 5b is directed radially inward and across the fragmentation opening 6b and into the thrombus 8b. In this embodiment, the liquid sprays 7 preferably emanate from the nozzles 5 at substantially the same time; however, in other embodiments, the liquid sprays 7 can emanate at different or alternating times or not at all based on user control over the thrombectomy system 100.

In any of the embodiments disclosed herein, the nozzle 5 (e.g. the output orifice thereof) can comprise any of a variety of shapes, for example, a circular shape (FIGS. 11B and 11C), an oval shape, a flattened shape (FIG. 11E), a fan shape, a rectangular shape, a square shape, a narrow shape, or a wide shape, or a wide, curved shape (FIG. 11D) or any other variation and/or combination of the foregoing. The foregoing various shapes of the nozzle 5 alter the shape and effect of the liquid spray 7. For example, a liquid spray 7 having a narrow shape and a small cross-sectional area can have greater fragmenting power but a smaller fragmenting surface area, whereas a liquid spray 7 having a fan shape (e.g., with a broad, flat cross-sectional profile that increases in breadth as it extends from the nozzle tip) can have reduced fragmenting power but a larger fragmenting surface area. In certain embodiments, the nozzle region 25 comprises a plurality of nozzles 5 (for example, FIG. 11E). An active portion 2 having multiple nozzles 5 is configured to have multiple liquid sprays 7 for fragmenting the thrombus 8.

Figure 12:
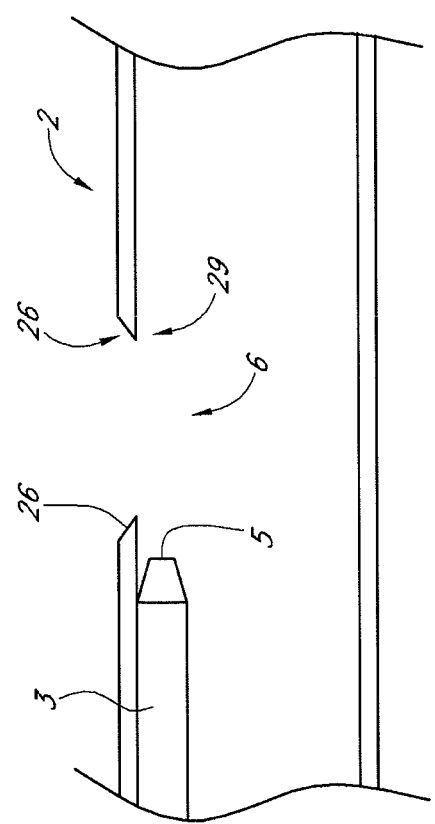
FIG. 12 is a longitudinal sectioned view of a fragmentation lumen having beveled edges along the sides of the fragmentation opening.

In any of the embodiments disclosed herein, the fragmentation opening 6 can comprise at least one beveled edge profile 26 (for example, FIG. 12). The beveled edge profile 26 can comprise a radiused cutting edge 26 as shown or an angled cutting edge. The surface of the beveled edge profile 26 can comprise without limitation, for example, a smooth, rough, ridged, abrasive or textured surface or any combination or variation thereof. Similar to the foregoing embodiments, the thrombus 8 is drawn into the fragmentation opening 6 by the vacuum in the suction lumen 4. During the fragmentation half-cycle, the beveled edge 26 assists the liquid spray 7 in fragmenting the thrombus 8 by providing a sharpened edge or surface against which the spray 7 pushes the thrombus 8. The beveled edge 26 can thus cut into the thrombus 8 on the side(s) remote from the liquid spray 7, providing enhanced fragmenting action.

In certain embodiments, at least a portion of the beveled edge profile 26 is configured to direct or send or transmit an ultrasonic wave into or through the contacted portion of the thrombus 8. In certain embodiments, the ultrasonic wave is configured to vibrate the thrombus 8 in order to dislodge at least a portion of the thrombus 8 from the vessel wall.

Figure 13:
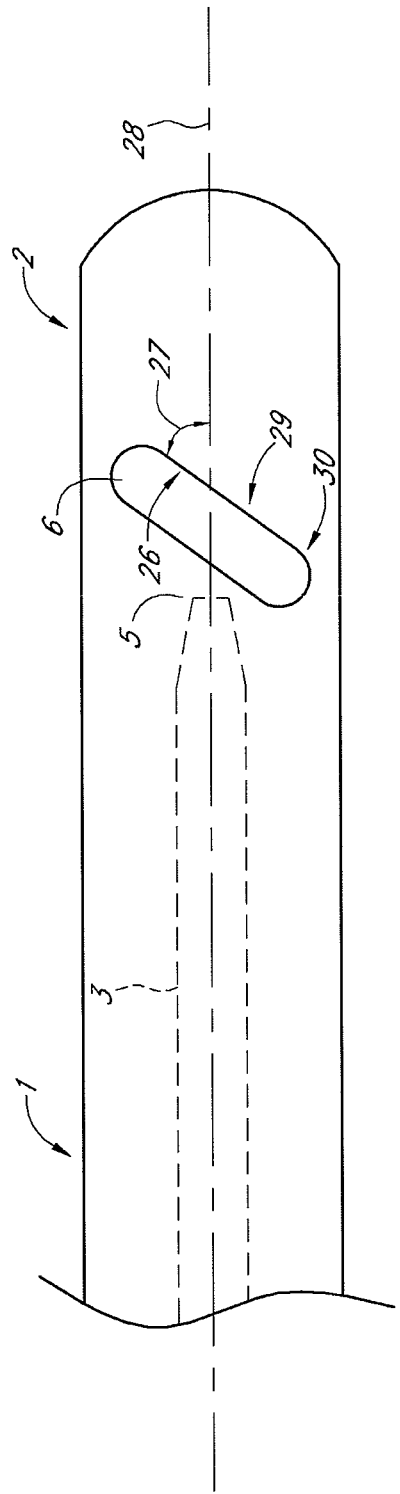
FIG. 13 is a partial top view of a fragmentation lumen having a fragmentation opening positioned at an angle to the longitudinal axis of the fragmentation lumen.

With reference to FIG. 13, in any of the embodiments of the thrombectomy system 100 disclosed herein, one or more of the fragmentation opening(s) 6 (or at least a distal edge 29 thereof) can be positioned or tilted or slanted at an angle 27 relative to a longitudinal axis 28 of the fragmentation lumen 3 or the catheter shaft 1. In certain embodiments, at least the distal edge 29 of such a fragmentation opening 6 comprises a beveled edge profile 26 as shown in FIG. 12. During the fragmentation half-cycle, the liquid spray 7 pushes the thrombus 8 against the slanted distal edge 29 such that a leading (generally proximally disposed) portion 30 of the distal edge 29 initiates a cut into the thrombus 8. As the thrombus is pushed against the distal edge 29, the cutting action proceeds distally from the leading portion 30 across the distal edge 30, in guillotine-like fashion, to effectively slice through the thrombus 8 with a reduction in the pushing force required from the fluid jet 7.

Figure 14:
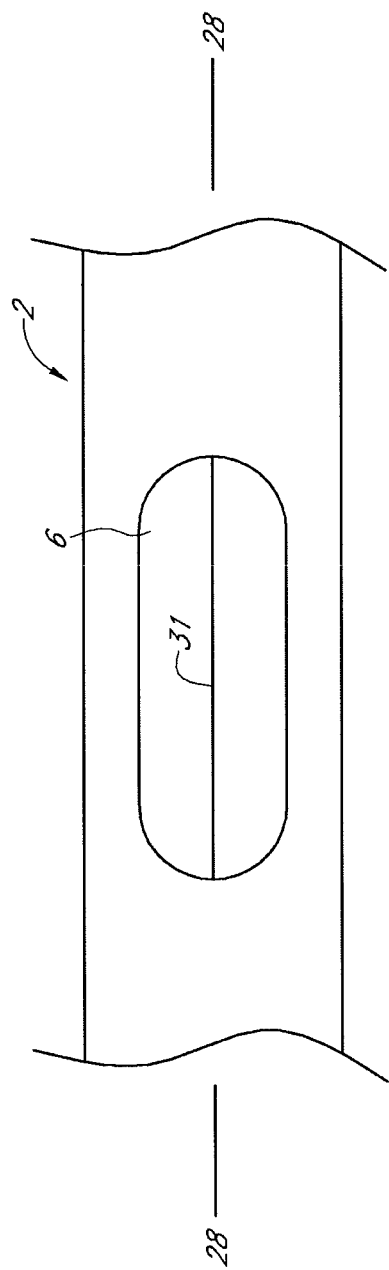
FIG. 14 is a partial top view of a fragmentation opening having a cutting member.
Figure 15:
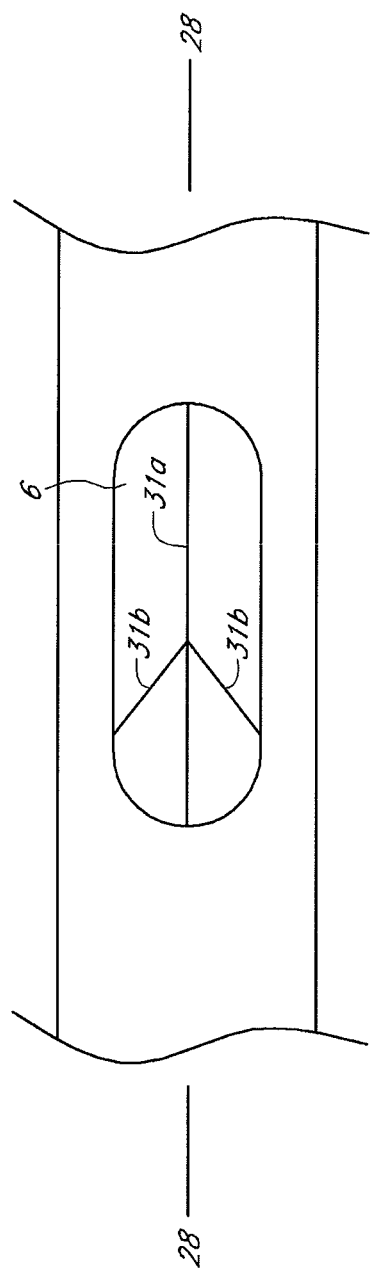
FIG. 15 is a partial top view of a fragmentation opening having multiple cutting members.

In any of the embodiments of the thrombectomy system 100 disclosed herein, the fragmentation opening 6 can comprise at least one cutting member 31 positioned or extending across the fragmentation opening 6 (for example, FIG. 14). In certain embodiments, the cutting member 31 is generally rigid and extends parallel or perpendicular or transverse to the longitudinal axis 28 of the fragmentation opening 6. In certain embodiments as shown in FIG. 15, the fragmentation opening 6 comprises at least one main cutting member 31a extending across the fragmentation opening 6, and at least one secondary cutting member 31b extending from one edge of the fragmentation opening 6 to the main cutting member 31a. In certain embodiments, the cutting member 31 is a wire or nylon member or the like suitably configured to fragment or cut or shear the thrombus 8. Preferably, the thrombus 8 is fragmented or cut or sheared by the cutting member 31 as the thrombus 8 is drawn into the fragmentation opening 6 by the vacuum within the suction lumen 4 during the suction half-cycle.

In any of the embodiments of the thrombectomy system 100 disclosed herein, the size and/or shape of the fragmentation opening 6 can be varied to suit the condition to be treated by the thrombectomy system 100. A smaller and/or thinner fragmentation opening 6 (e.g. a slit configuration as in FIG. 13) is can be used when treating or removing a harder or tougher thrombus 8 because such a fragmentation opening 6 allows only a small portion of the thrombus 8 to pass across the liquid spray 7 thereby allowing the liquid spray 7 to more easily fragment the thrombus 8.

Figure 16:
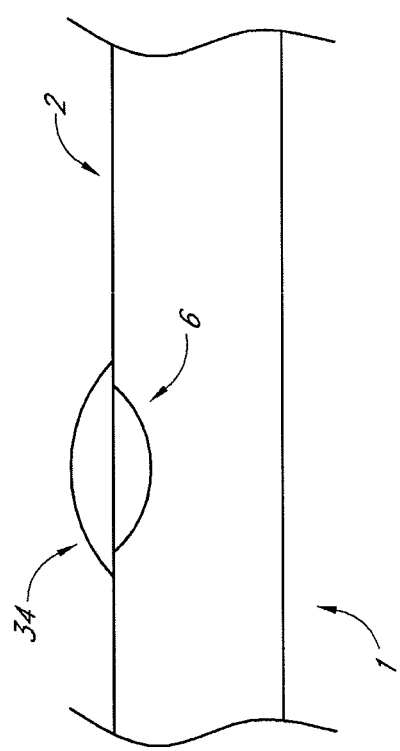
FIG. 16 is a longitudinal sectioned view of a fragmentation lumen comprising a standoff member.

In certain embodiments (see, e.g., FIG. 17), the active portion 2 is configured to preserve vessel valves 33 and/or avoid drawing the vessel wall 32 away from adjacent tissues while removing the thrombus 8. In the depicted embodiment of FIGS. 16 and 17, the active portion 2 comprises a standoff member 34 which is positioned or extends over the fragmentation opening 6 to facilitate a method of removing the thrombus while preserving or avoiding damage to the vessel valves 33 and/or avoiding drawing the vessel wall 32 away from adjacent tissues. The standoff member 34 is configured to deflect the vessel valve 33 away from the fragmentation opening 6 (see, e.g., FIG. 17) while the thrombus 8 is drawn into the fragmentation opening 6 due to the vacuum in the active portion 2 during the suction half-cycle.

The standoff member 34 can comprise, in various embodiments, a cross member that extends across the fragmentation opening 6 and can extend radially outward therefrom, e.g., a wire cage or dome, a wire or nylon mesh dome, a perforated dome, one or more arched wire(s) or other member(s), or the like. The standoff member 34 can be configured to allow thrombus 8 material to pass through the standoff member 34 while preventing vessel wall 32 tissue, vessel valve 33 tissue or the like from entering the fragmentation opening 6. The standoff member 34 is advantageous in that it tends to preserve the structure of and prevents damage to the vessel valve 33 tissue or vessel wall 32 or the like. The standoff member 34 also tends to prevent the fragmentation opening 6 from adhering to the nearest vessel wall 32 or the like, thereby providing the operator more control over the thrombectomy system 100.

In certain embodiments, multiple standoff members 34 or a single standoff member 34 that surrounds the active portion 2, can be employed to prevent the collapse of the vessel wall and preserve any native valves as discussed above.

In some embodiments, the catheter 1 comprises at least one support member located near the active portion 2 (and preferably opposite the fragmentation opening(s)) to facilitate positioning the active portion 2 against the surgical site or into the thrombus 8. The support member can comprise, for example, an inflatable/collapsible balloon, a deployable/retractable arm, or other means or mechanisms for urging the active portion 2 and the fragmentation opening 6 against the surgical site or the thrombus 8.

Figure 17:
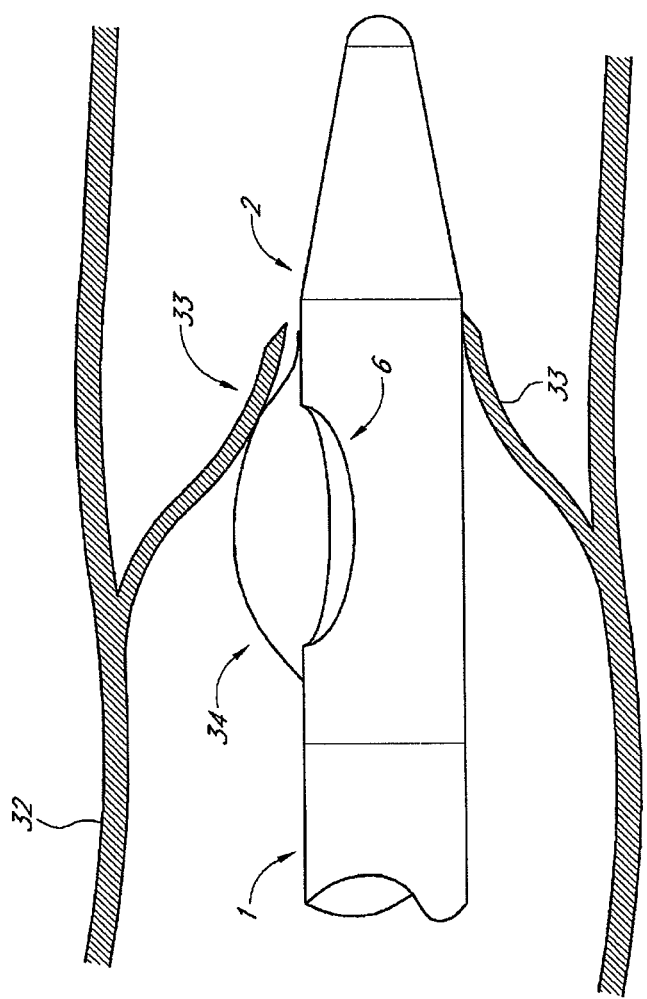
FIG. 17 is a longitudinal sectioned view of the operation of a thrombectomy system having a standoff member configured for valve preservation.

In any of the embodiments of the thrombectomy system 100 discussed herein, the catheter system 101 can further optionally comprise a curved active portion 35 as shown in FIG. 18 as a further alternative to facilitate a method of removing the thrombus 8 while preserving or avoiding damage to the vessel valve(s) 33 or vessel walls 32 (see FIG. 17). In the depicted embodiment, the distal end of the catheter shaft 1 is curved radially outward in the region distally beyond the fragmentation opening 6, toward the side wherein the fragmentation opening 6 exists. In other embodiments, the distal end of the shaft 1 is curved radially outward on the side opposite the fragmentation opening 6. The curved distal end of the shaft 1, as depicted in FIG. 18, is configured to position the fragmentation opening 6 away from any nearby vessel valve(s) 33 and/or the vessel wall 32, thereby preventing or minimizing damage to the valve(s) 33 and/or wall 32 during operation of the thrombectomy system 100.

The curved active portion 35 can also facilitate a method of sweeping out a larger portion of the vessel volume when the operator turns or twists the curved fragmentation lumen 35 and/or the catheter system 101. The curved active portion 35 facilitates greater access to the target treatment area of the vessel. In some embodiments, the curvature of the curved fragmentation lumen 35 is variable, e.g. via steerer wire(s) or the like built into the catheter shaft 1, or a stiff distal sheath that can be retracted to expose the curved distal portion of the catheter 101, which recovers at least a portion of its curved configuration upon such exposure.

Figure 19A:
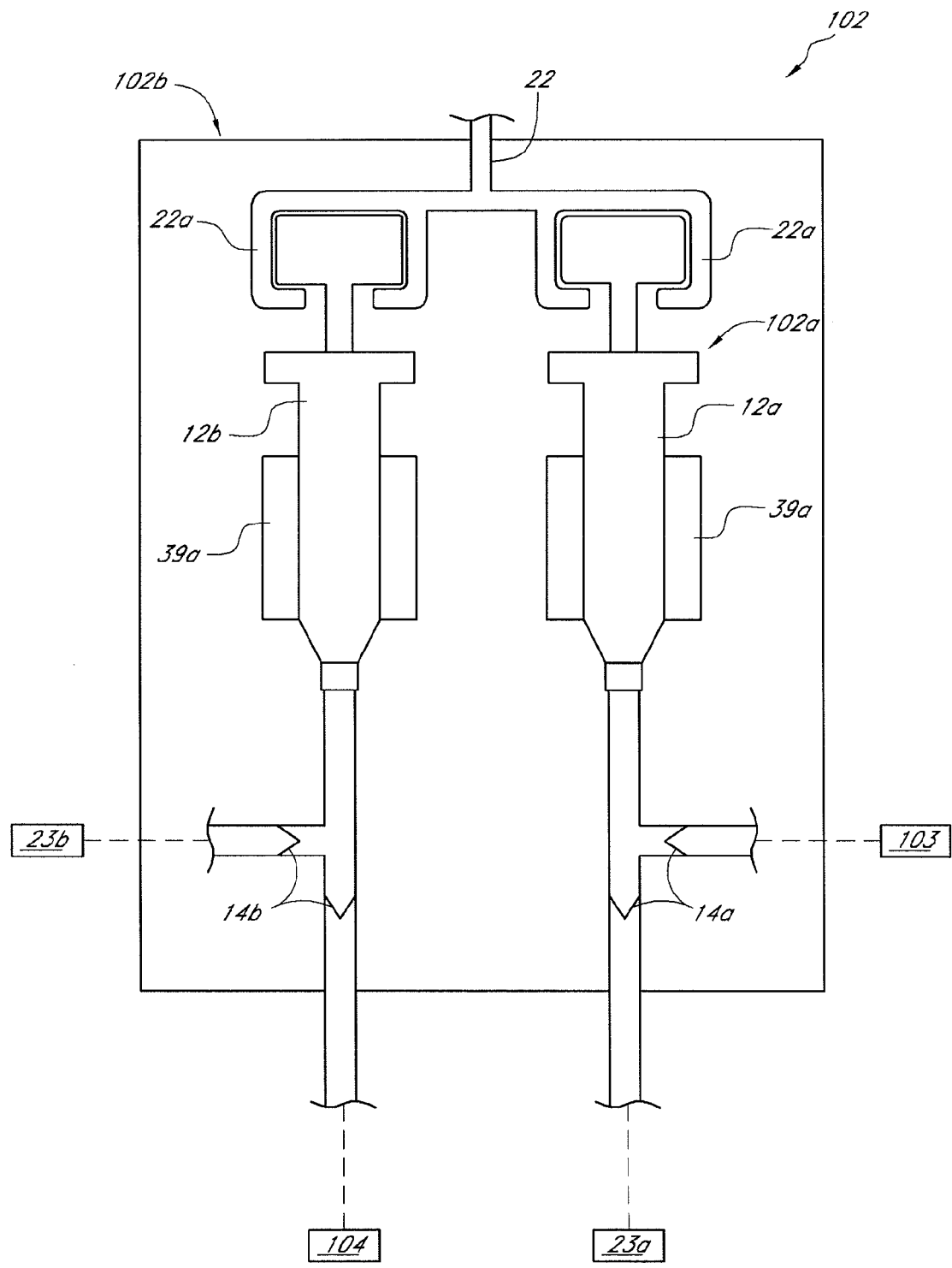
FIG. 19A is a longitudinal sectioned view of a disposable pump syringes.
Figure 19B:
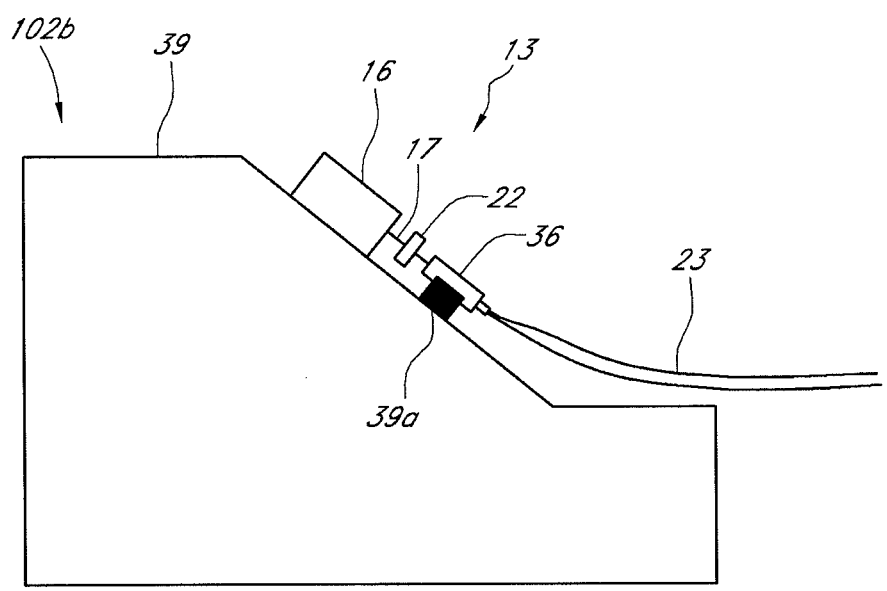
FIG. 19B is a side view of the reusable housing or base.

With reference to FIGS. 19A-19B, in any of the embodiments of the thrombectomy system 100 described herein, the drive unit 102 can optionally comprise a disposable, single-use, limited-use, or single-patient-use module 102a that is releasably connected or engaged with a reusable drive module 102b. The depicted version of the disposable module 102a comprises disposable syringes (either custom made or standard off the shelf components) that serve as the fragmentation pump 12a and suction pump 12b. Where employed, the syringe(s) 12a, 12b are releasably connected or engaged with the reusable drive module 102b. In the depicted configuration, the drive module 102b includes the dual pump actuator 22 and the motor system 13 that drives the actuator 22. The syringes 12a, 12b can each comprise a piston and a cylinder, wherein the retraction of the piston draws fluid or other materials into the cylinder, and the advancement of the piston expels fluid and other materials from the cylinder.

In the depicted embodiment, the reusable drive module 102b can further comprise a base 39 on which is mounted the motor system 13 including the motor 16 and linkage mechanism 17, and the actuator 22. The base 39 can further comprise one or more syringe holders 39a to hold the syringe(s) 12a, 12b securely and releasably with respect to the base 39. The actuator 22 includes one or more plunger clips 22a that interface with the plunger(s) of the syringes(s) 12a, 12b such that, upon installation of the syringes 12a, 12b in the holders 39a, the clips 22a receive the syringe plungers and thereby facilitate driving the pistons of the syringes 12a, 12b via the motor system 13.

In the embodiment of the thrombectomy system 100 depicted in FIGS. 19A-19B, the disposable module 102a (including the syringes 12a, 12b) of the drive system 102, and the catheter system 101 and tubing system 105 can be combined as a single disposable unit. Such a disposable module can be releasably connected to the reusable drive module 102b and to a suitable liquid source 103 and waste receptacle 104, used to treat one or several patients according to any of the methods disclosed herein, removed from the drive module 102b after such use, and discarded. The disposable module can optionally further comprise the liquid source 103 and/or the waste receptacle 104. In either case, the disposable module 102a can optionally be packaged as a kit, in a sterile package, to facilitate convenient storage and clinical use. In the sterile package, the kit comprising the disposable module 102a can be completely or partially pre-assembled, or completely disassembled.

A further embodiment of the thrombectomy system 100 is schematically depicted in FIG. 20, wherein the drive unit 102 comprises a pneumatic drive unit 40 that is connectable to a pneumatic power source 18. The pneumatic drive unit 40 can comprise a pneumatic drive motor 20, pump(s) 12 (for example, the dual pumps 12a, 12b of FIGS. 1 and 19), a linkage mechanism 17 (for example, the linkage mechanism 17 of FIG. 1), and a pneumatic hose 41 that is connectable to the pneumatic power source 18. The pneumatic power source 18 can comprise, for example, a facility pressurized air system, an air compressor, a compressed air tank or any other suitable compressed air source; and the pneumatic motor 20 can comprise a reciprocating pneumatic drive, a turbine, or any other suitable pneumatic drive system. Accordingly, the pneumatic motor 20, under power delivered via the pneumatic hose 41, outputs mechanical drive motion via, for example, the linkage mechanism 17 which can reciprocate as depicted, or via any other suitable power delivery system, such as a rotating shaft, gear(s), drive chain, belt, etc.

A reciprocating output, as depicted in FIG. 20, is suitable for driving reciprocating pump(s), which can comprise the pumps 12a, 12b described elsewhere herein. In one embodiment, as described herein, the pumps 12a, 12b can comprise syringe pumps. The thrombectomy system 100 of FIG. 20 can further comprise the tubing system 105, in any of the variations thereof described herein, including, for example, the fragmentation tubing 23a, the suction tubing 23b, the liquid source tubing 23c, and the waste tubing 23d. The fragmentation tubing 23a and the suction tubing 23b connect the catheter system 101 to the pneumatic drive unit 40. The fragmentation tubing 23a conducts pressurized liquid to the catheter system 101 whereas the suction lumen 23b provides suction to the catheter system 101. The liquid source tubing 23c connects the pneumatic drive unit 40 to the liquid source 103 whereas the waste tubing 23d connects the pneumatic drive unit 40 to the waste receptacle 104. The catheter system 101 can comprise the catheter system illustrated in FIG. 1 or other any other embodiment herein disclosed, or any other suitable catheter system.

The thrombectomy system 100 depicted in FIG. 20 can comprise a single disposable unit, e.g. a self-contained disposable thrombectomy system. Such a disposable thrombectomy system can be connected to the pneumatic power source 18 and to a suitable liquid source 103 and waste receptacle 104, used to treat one or several patients according to any of the methods disclosed herein, removed from the pneumatic power source 18 after such use, and discarded. The self-contained disposable thrombectomy system 100 (e.g., including at least the pneumatic drive unit 40, the catheter system 101 and the tubing 23a, 23b), can optionally further comprise the liquid source 103 and/or the waste receptacle 104, and the corresponding tubing 23c and/or 23d. In either case, the disposable thrombectomy system 100 can optionally be packaged as a kit, in a sterile package, to facilitate convenient storage and clinical use. In the sterile package, the kit comprising the thrombectomy system 100 can be completely or partially pre-assembled, or completely disassembled.

In some techniques, the thrombectomy system 100 can function as follows. During a first portion of an operating cycle (for example, the fragmentation half-cycle) the system 100 applies positive pressure (e.g., a distally-directed pressure) to liquid in a pressure lumen of a shaft sized for insertion into a blood vessel lumen. The pressure lumen can comprise, for example, any of the fragmentation lumens 3 depicted in FIG. 2-10, or 12-13. The shaft can comprise, for example, any of the shafts 1 disclosed herein. The liquid under pressure is directed through a nozzle 5 (for example, FIGS. 2-13) to create a liquid spray 7 (for example, FIGS. 4, 6, 8, 10). Then, during a second portion of the operating cycle (for example, the suction half-cycle), the thrombectomy system 100 applies a negative pressure (e.g., a proximally-directed pressure) to liquid in a suction lumen of the shaft. The suction lumen can comprise but is not limited to any of the suction lumens 4 illustrated in FIGS. 2-10. The negative pressure applied to the suction lumen evacuates liquid and other materials within the suction lumen and into the waste receptacle 104. The thrombectomy system 100 ceases to apply negative pressure or additional negative pressure to the suction lumen during the first portion of the operating cycle. Additionally, during the second portion of the operating cycle, the thrombectomy system 100 ceases to apply positive pressure or additional positive pressure to the pressure lumen. The foregoing operating cycle can be repeated a plurality of times.

In other techniques, the thrombectomy system 100 can function as follows. The system 100 delivers liquid through a fragmentation lumen of an elongate shaft sized for insertion into a blood vessel at a peak pressure of 100 PSI or less. Additionally, the thrombectomy system 100 emits the liquid as a liquid spray from the fragmentation lumen. Near the liquid spray, the thrombectomy system applies a suction via an evacuation lumen of the elongate shaft. As illustrated in FIGS. 1-10, the shaft 1 can comprise a fragmentation lumen 3 and a suction lumen 4, wherein pressurized liquid is delivered through the fragmentation lumen to generate a liquid spray through a nozzle 5. In some embodiments, the liquid spray emanates across the fragmentation opening 6 as depicted in FIGS. 6 and 10, and the vacuum applied to the suction lumen 4 evacuates the liquid and other materials from the suction lumen 4.

In certain techniques, the thrombectomy system 100 can be used as follows for removing occlusive material, such as a thrombus 8, from a blood vessel, e.g. as depicted in FIGS. 2-10. Such a method of removing occlusive material can comprise inserting an elongate shaft (for example, any of the shafts 1 of FIGS. 1-8) into the blood vessel, wherein the shaft comprises a pressure lumen and an evacuation lumen. Additionally, the method can comprise applying negative pressure via the evacuation lumen to draw a portion of the occlusive material near the pressure lumen. The method can further comprise emitting a liquid spray from the pressure lumen by delivering liquid through the pressure lumen at a peak pressure of less than 100 PSI, and fragmenting the portion of occlusive material with the liquid spray. The pressure lumen can comprise, for example, any of the fragmentation lumens 3 depicted in FIG. 2-10, or 12-13. The suction lumen can comprise, for example, any of the suction lumens 4 illustrated in FIGS. 2-10.

In other techniques for removing occlusive material from a blood vessel, a method comprises inserting an elongate shaft (e.g. any of the shafts 1 disclosed herein) into the blood vessel, wherein the shaft has a pressure lumen and an evacuation lumen. Additionally, the method can comprise applying, in alternating fashion, positive pressure (e.g., distally-directed pressure) to the pressure lumen and negative pressure (e.g., proximally-directed pressure) to the evacuation lumen, and drawing a portion of the occlusive material into the shaft via the negative pressure. The method further can further comprise fragmenting the drawn portion of occlusive material via the positive pressure.

The foregoing techniques (as well as the other methods disclosed herein) for removing occlusive material can be used to treat any type of occlusion in any type of blood vessel including without limitation, for example, arteries, veins (including deep veins), or other similar vessels as well as vessels having or comprising an implanted stent, graft, or shunt. The various disclosed embodiments of the thrombectomy system 100 can be employed in these techniques and methods. Furthermore, the foregoing techniques (as well as the other methods disclosed herein) can be used to treat deep vein thrombosis, and the various disclosed embodiments of the thrombectomy system 100 can be employed in such techniques and methods.

Additional embodiments comprise methods of sterilization. Certain such methods can comprise sterilizing, either terminally or sub-terminally, any of the apparatus disclosed herein that are intended for insertion into (or other contact with) the patient or that are intended for use at or near the surgical field during treatment of a patient. Any suitable method of sterilization, whether presently known or later developed, can be employed.

Accordingly, certain methods comprise sterilizing, either terminally or sub-terminally, any of the embodiments of the thrombectomy system 100 or any of the components or subsystems thereof disclosed herein, including but not limited to any of the embodiments of the disposable module 102a disclosed herein. Any suitable method of sterilization, whether presently known or later developed, can be employed. For example, the method can comprise sterilizing any of the above-listed apparatus with an effective dose of a sterilant such as cyclodextrin (Cidex™), ethylene oxide (EtO), steam, hydrogen peroxide vapor, electron beam (E-beam), gamma irradiation, x-rays, or any combination of these sterilants.

The sterilization methods can be performed on the apparatus in question while the apparatus is partially or completely assembled (or partially or completely disassembled); thus, the methods can further comprise partially or completely assembling (or partially or completely disassembling) the apparatus before applying a dose of the selected sterilant(s). The sterilization methods can also optionally comprise applying one or more biological or chemical indicators to the apparatus before exposing the apparatus to the sterilant(s), and assessing mortality or reaction state of the indicator(s) after exposure. As a further option, the sterilization methods can involve monitoring relevant parameters in a sterilization chamber containing the apparatus, such as sterilant concentration, relative humidity, pressure, and/or apparatus temperature.

In view of the foregoing discussion of methods of sterilization, further embodiments comprise sterile apparatus. Sterile apparatus can comprise any of the apparatus disclosed herein that are intended for insertion into (or other contact with) the patient or that are intended for use at or near the surgical field during treatment of a patient. More specifically, any one or combination of the following can be provided as a sterile apparatus: any of the embodiments of the thrombectomy system 100 or any of the components or subsystems thereof disclosed herein, including but not limited to any of the embodiments of the disposable module 102a disclosed herein.

Although the foregoing disclosure has been described in terms of certain embodiments, other embodiments will be apparent to those of ordinary skill in the art from the disclosure herein. Moreover, the described embodiments have been presented by way of example only, and are not intended to limit the scope of the invention(s). Indeed, the novel methods and systems described herein may be embodied in a variety of other forms without departing from the spirit thereof. Accordingly, other combinations, omissions, substitutions and modifications will be apparent to the skilled artisan in view of the disclosure herein.

What is claimed is:

1. Apparatus for removing occlusive material from a blood vessel lumen, said apparatus comprising:
a catheter shaft sized for insertion into said blood vessel, said shaft having a pressure lumen terminating in a nozzle and an evacuation lumen having a fragmentation opening adjacent said nozzle;
a liquid source configured for flowing liquid through said pressure lumen; and
a drive unit connected to said evacuation and pressure lumens and comprising:
a pressure pump configured to deliver positive pressure impulses to said pressure lumen;
a suction pump configured to deliver negative pressure impulses to said evacuation lumen; and
a dual-piston actuator configured to drive the pressure pump and the suction pump to cause a cycling pressure pattern in which the positive pressure impulses in said pressure lumen alternate with the negative pressure impulses in said evacuation lumen;
wherein said nozzle of said pressure lumen is positioned relative to said fragmentation opening in said evacuation lumen such that occlusive material cut or fragmented by liquid spraying out of said nozzle in response to said positive pressure impulses enters said evacuation lumen through said fragmentation opening.

2. The apparatus of claim 1 wherein said positive pressure impulses have a peak pressure of between 20 and 100 PSI.

3. The apparatus of claim 2, wherein said positive pressure impulses have a peak pressure of between 30 and 70 PSI.

4. The apparatus of claim 1, wherein said negative pressure impulses create a vacuum of 50 mmHg or greater in said evacuation lumen.

5. The apparatus of claim 1, wherein:
said nozzle comprises a tapered nozzle portion configured to direct a liquid spray toward an interior portion of the catheter shaft.

6. The apparatus of claim 5, wherein:
said catheter shaft further comprises a sidewall having a sidewall opening; and
said tapered nozzle portion is configured to direct the liquid spray alongside said sidewall opening.

7. The apparatus of claim 5, wherein:
said catheter shaft further comprises a sidewall having a sidewall opening; and
said tapered nozzle portion is configured to direct the liquid spray alongside or through said sidewall opening and distally from said pressure lumen.

8. The apparatus of claim 1, wherein:
said nozzle comprises a nozzle portion having a reduced luminal cross-sectional area relative to a proximal portion of said pressure lumen; and
said catheter shaft further comprises a sidewall with a sidewall opening; and
said nozzle portion is configured to deliver a liquid spray that passes alongside said sidewall opening.

9. The apparatus of claim 1, wherein said nozzle comprises a nozzle portion having a generally circular exit port.

10. The apparatus of claim 1, wherein said nozzle comprises a nozzle portion having an exit port with a flattened shape.

11. The apparatus of claim 1, further comprising a first check valve positioned between the liquid source and the pressure pump to permit only one way flow from the liquid source to the pressure pump.

12. The apparatus of claim 11, further comprising a second check valve positioned between a waste receptacle and said suction pump to permit only one way flow from the suction pump to the waste receptacle.

13. The apparatus of claim 1, wherein the dual-piston actuator is configured to vary a speed of the alternating between the positive pressure impulses and the negative pressure impulses based on whether material is detected in the evacuation lumen or within the fragmentation opening.

14. A method of removing occlusive material from a blood vessel, said method comprising:
inserting an elongate shaft into said blood vessel, said shaft having a pressure lumen and an evacuation lumen;
causing, by a drive unit, a cycling pressure pattern to be applied to said pressure lumen and said evacuation lumen, whereby a positive pressure applied to said pressure lumen alternates with a negative pressure applied to said evacuation lumen, and wherein the drive unit comprises a pressure pump configured to deliver the positive pressure to the pressure lumen, a suction pump configured to deliver the negative pressure to the evacuation lumen, and a dual-piston actuator configured to drive the pressure pump and the suction pump to cause the cycling pressure pattern;
drawing a portion of said occlusive material toward said pressure lumen in response to the application of the negative pressure to said evacuation lumen;
emitting a liquid spray from said pressure lumen in response to the application of the positive pressure to said pressure lumen; and
fragmenting said portion of occlusive material with said liquid spray.

15. The method of claim 14, further comprising evacuating said fragmented material via said evacuation lumen.

16. The method of claim 14, wherein said liquid spray is emitted from said pressure lumen at a peak pressure of less than 100 PSI.

17. The method of claim 16, wherein said peak pressure is 30-50 PSI.

18. The method of claim 14, further comprising causing said cycling pressure pattern using a drive unit comprising a dual-piston actuator driving a pressure pump and a suction pump.

19. The method of claim 18, further comprising sealing said pressure pump using at least one check valve.

20. The method of claim 19, further comprising sealing said suction pump using a second at least one check valve.

21. The method of claim 18, further comprising sealing said suction pump using at least one check valve.

22. A method comprising:
delivering liquid through a fragmentation lumen of an elongate shaft at a positive pressure of 100 PSI or less, the elongate shaft sized for insertion into a blood vessel;
emitting said liquid as a liquid spray from said fragmentation lumen; and
applying a negative pressure to said liquid spray via an evacuation lumen of said elongate shaft;
wherein the positive pressure applied to the fragmentation lumen alternates with the negative pressure applied to the evacuation lumen via a drive unit comprising a pressure pump configured to apply the positive pressure to the fragmentation lumen, a suction pump configured to apply the negative pressure to the evacuation lumen, and a dual-piston actuator configured to drive the pressure pump and the suction pump to cause a cycling pressure pattern applied to the fragmentation lumen and the evacuation lumen.

23. The method of claim 22, wherein said delivering comprises delivering said liquid at a peak pressure of 20-70 PSI.

24. The method of claim 22, wherein said delivering comprises delivering said liquid at a peak pressure of 30-50 PSI.

25. The method of claim 22, wherein said applying said negative pressure creates a vacuum of 50 mmHg or more.

26. The method of claim 22, further comprising evacuating material fragmented by said liquid spray via said evacuation lumen.

27. The method of claim 22, wherein said positive and negative pressures respectively applied to the fragmentation and evacuation lumens are created by a drive unit comprising a dual-piston actuator driving a pressure pump and a suction pump.

* * * * *